(12) United States Patent
Packirisamy et al.

(10) Patent No.: US 8,926,906 B2
(45) Date of Patent: Jan. 6, 2015

(54) MICROFLUIDIC DEVICE AND METHOD FOR FABRICATING THE MICROFLUIDIC DEVICE

(75) Inventors: Muthukumaran Packirisamy, Pierrefonds (CA); Ashwin L. Acharya, Edmonton (CA)

(73) Assignee: Concordia University, Montreal (CA)

( * ) Notice: Subject to any disclaimer, the term of this patent is extended or adjusted under 35 U.S.C. 154(b) by 325 days.

(21) Appl. No.: 13/055,364

(22) PCT Filed: Jul. 21, 2009

(86) PCT No.: PCT/CA2009/001014
§ 371 (c)(1),
(2), (4) Date: Apr. 7, 2011

(87) PCT Pub. No.: WO2010/009543
PCT Pub. Date: Jan. 28, 2010

(65) Prior Publication Data
US 2011/0262307 A1    Oct. 27, 2011

Related U.S. Application Data

(60) Provisional application No. 61/082,302, filed on Jul. 21, 2008.

(51) Int. Cl.
| | | |
|---|---|---|
| *G01N 21/00* | (2006.01) | |
| *G01N 21/64* | (2006.01) | |
| *G01N 21/05* | (2006.01) | |
| *C12M 1/00* | (2006.01) | |
| *G01N 21/76* | (2006.01) | |
| *G01N 21/03* | (2006.01) | |

(52) U.S. Cl.
CPC .............. *G01N 21/645* (2013.01); *G01N 21/05* (2013.01); *G01N 21/6428* (2013.01); *G01N 2021/0325* (2013.01); *G01N 2021/056* (2013.01); *G01N 2021/6417* (2013.01); *G01N 2021/6439* (2013.01); *G01N 2021/6484* (2013.01); *G01N 2201/062* (2013.01); *G01N 2201/08* (2013.01); *G01N 2021/0346* (2013.01)

USPC .................. 422/82.08; 422/82.05; 422/82.06; 422/82.07; 436/164; 436/172; 435/283.1; 435/288.7

(58) Field of Classification Search
None
See application file for complete search history.

(56) References Cited

U.S. PATENT DOCUMENTS 5,580,784 A * 12/1996 Berndt ........................ 435/288.7
5,914,041 A    6/1999 Chancellor
(Continued)

FOREIGN PATENT DOCUMENTS

WO            00/68671 A2      11/2000
WO         2005/108963         11/2005
(Continued)

OTHER PUBLICATIONS

International Search Report, PCT/CA2009/001014, dated Oct. 5, 2009, 4 pages.
(Continued)

*Primary Examiner* — Neil N Turk
(74) *Attorney, Agent, or Firm* — Senniger Powers LLP

(57) ABSTRACT

The present application is directed to a technological platform with integrated microfluidic and optical modules for bio-detection. The platform enables in-situ detection by integrating fluidics with optical source and detection capabilities within a fabricated microchip. The platform is a polymer-based microfluidic chip having integrated excitation source and detection elements in a vicinity of a microfluidic reaction chamber configured to contain a micro-volume of a test sample. The principle of detection is based on an excitation source induced fluorescence of the test sample within the microfluidic reaction chamber.

17 Claims, 14 Drawing Sheets

(56) References Cited

U.S. PATENT DOCUMENTS

| | | |
|---|---|---|
| 6,197,503 B1 | 3/2001 | Vo-Dinh et al. |
| 6,448,064 B1 | 9/2002 | Vo-Dinh et al. |
| 6,734,436 B2 | 5/2004 | Faris et al. |
| 6,878,755 B2 | 4/2005 | Singh et al. |
| 7,157,053 B2 | 1/2007 | Hahn et al. |
| 7,214,298 B2 | 5/2007 | Spence et al. |
| 7,486,387 B2 | 2/2009 | Fritz |
| 2003/0235924 A1 | 12/2003 | Adams et al. |
| 2004/0208792 A1 | 10/2004 | Linton et al. |
| 2004/0219661 A1 | 11/2004 | Chen et al. |
| 2005/0130226 A1* | 6/2005 | Ahn et al. ............ 435/7.1 |
| 2005/0213868 A1* | 9/2005 | Cunningham ............ 385/12 |
| 2006/0063160 A1 | 3/2006 | West et al. |
| 2006/0068412 A1 | 3/2006 | Tang et al. |
| 2006/0099705 A1* | 5/2006 | Wikswo et al. ............ 435/288.5 |
| 2006/0227325 A1* | 10/2006 | Rulison et al. ............ 356/401 |
| 2007/0070347 A1 | 3/2007 | Scherer et al. |
| 2008/0213821 A1 | 9/2008 | Liu et al. |

FOREIGN PATENT DOCUMENTS

| | | |
|---|---|---|
| WO | 2007002560 A1 | 1/2007 |
| WO | 2007/021815 A2 | 2/2007 |
| WO | 2007/054710 A2 | 5/2007 |
| WO | 2007/077218 A1 | 7/2007 |

OTHER PUBLICATIONS

Written Opinion, PCT/CA2009/001014, dated Oct. 5, 2009, 4 pages.

S.J. Hart, R.D. Jiji, "A simple, low-cost, remote fiber-optic micro volume fluorescence flowcell for capillary flow-injection analysis", Analytical and Bioanalytical Chemistry 374 (2002), pp. 385-389.

T. Zhang, Q. Fang, S. Wang, Z. Fang, "Enhancement of Signal-To-Noise Levels by Synchronized Dual Wavelength Modulation for Light Emitting Diode Fluorimetry in Microfluidic Systems", µTAS 2003, Seventh International Conference on Micro Total Analysis Systems, USA, Oct. 5-9, 2003.

V. Namasivayam, R. Lin, B. Johnson, S. Brahmasandra, Z. Razzacki, D.T. Burke, M.A. Burns, "Advances in on-chip photodetection for applications in miniaturized genetic analysis systems", Journal of Micromechanics and Microengineering 14 (2004), pp. 81-90.

M.L. Chabinyc, D.T. Chiu, J.C. McDonald, A.D. Stroock, J.F. Christian, A.M. Karger, G.M. Whitesides, "An integrated fluorescence detection system in poly(dimethylsiloxane) for microfluidic applications", Analytical Chemistry 73 (2001), pp. 4491-4498.

J.S. Kuo, C.L. Kuyper, P.B. Allen, G.S. Fiorini, D.T. Chiu, "High-power blue/UV light-emitting diodes as excitation sources for sensitive detection", Electrophoresis 25 (2004), pp. 3796-3804.

N.Y. Kwok, S. Dong, W. Lo, K.Y. Wong, "An optical biosensor for multi-sample determination of biochemical oxygen demand(BOD)", Sensors and Actuators B: Chemical 110 (2005), pp. 289-298.

A. Suzuki, J. Kondoh, Y. Matsui, S. Shiokawa, K. Suzuki, "Development of novel optical waveguide surface plasmon resonance(SPR) sensor with dual light emitting diodes", Sensors and Actuators B: Chemical 106 (2005), pp. 383-387.

V. Srinivasan, V.K. Pamula, R.B. Fair, "Droplet-based microfluidic lab-on-a-chip for glucose detection", Analytica Chimica Acta 507 (2004), pp. 145-150.

D. Stadnik, A. Dybko, "Fibre optic coupler as a detector for microfluidic applications", The Analyst 128 (2003), pp. 523-526.

M. Sun, W.B. Du, Q. Fang, "Microfluidic liquid—liquid extraction system based on stopped-flow technique and liquid core waveguide capillary", Talanta 70 (2006), pp. 392-396.

J. Seo, L.P. Lee, "Disposable integrated microfluidics with self-aligned planar microlenses", Sensors and Actuators B: Chemical 99 (2004), pp. 615-622.

F. Dang, L. Zhang, M. Jabasini, N. Kaji, Y. Baba, "Characterization of electrophoretic behavior of sugar isomers by microchip electrophoresis coupled with videomicroscopy", Analytical Chemistry 75 (2003), pp. 2433-2439.

A. Gulliksen, L. Solli, F. Karlsen, H. Rogne, E. Hovig, T. Nordstrom, R. Sirevag, "Real-time nucleic acid sequence-based amplification in nanoliter volumes", Analytical Chemistry 76 (2004), pp. 9-14.

L.J. Lucas, J.H. Han, J. Chesler, J.Y. Yoon, "Latex immunoagglutination assay for a vasculitis marker in a microfluidic device using static light scattering detection", Biosensors & bioelectronics 22 (2007), pp. 2216-2222.

"Information about Dow Corning® brand Silicone Encapsulants, Dow Corning Corp., Midland, MI", http://www.dowcorning.com.

Miyaki, Kyo et al., "Fabrication of an integrated PDMS microchip incorporating an LED-induced fluorescence device", Anal Bioanal Chem, vol. 382, May 10, 2005, pp. 810-816.

* cited by examiner

MICROFLUIDIC DEVICE AND METHOD FOR FABRICATING THE MICROFLUIDIC DEVICE

RELATED APPLICATIONS

This application claims the benefit of and is a National Phase Entry of International Application Number PCT/CA2009/001014 filed Jul. 21, 2009, and claims the benefit of U.S. Provisional Patent Application No. 61/082,302 filed on Jul. 21, 2008, which are both hereby incorporated by reference in their entirety.

FIELD OF THE INVENTION

The invention relates to a microfluidic device for use in excitation induced fluorescence testing.

BACKGROUND OF THE INVENTION

The field of integrated Micro-Electro-Mechanical Systems (MEMS) including microfluidics, microelectronics and photonics offers a vast potential to realize low cost, efficient and reliable means of sensing. This field has recently attracted remarkable attention due to its potential of implementing novel applications in numerous areas. Investigation into the use of MEMS technology to produce microdevices for biological applications, namely, Bio MicroElectro Mechanical Systems (BioMEMS) has increased recently in the hopes of developing opportunities and commercializing devices in the areas of medicine, life sciences, bio-security and Point-Of-Care (POC) diagnosis and drug delivery.

Device portability is considered to be an important feature for in-situ medical detection applications. Miniaturization of a biosensor is also considered to be important for ease of device handling, utilizing smaller sample volumes and assisting in rapid or simple biological detection leading to high throughput.

In the past decade, BioMEMS applications in the area of microfluidics have received enormous attention due to a) the availability of suitable fabricating methodologies to make individual and/or integrated devices, b) the quest for less expensive and portable devices to perform simple and quick analysis and c) the potential of micro-systems for use in performing fundamental studies of physical, chemical and biological processes in micro-level test samples. A majority of work carried out on microfluidic devices has involved the biomedical field, especially in the life sciences and diagnostics domain—POC analysis, Micro Total Analysis Systems (µTAS), DNA and proteomic chips, protein chips and cell chips. Applications include separation of proteins and amino acids, high throughput DNA analysis, cell culture and handling, clinical diagnostics and immunoassays.

SUMMARY OF THE INVENTION

According to an aspect of the present invention, there is provided a polymer-based microfluidic device for detecting induced fluorescence in a micro-volume of a fluid, the device comprising: a top portion comprising: a wavelength specific excitation source for inducing fluorescence in the fluid; a lens for collecting emitted fluorescence from the fluid; a bottom portion; a chamber having walls bounded by the top portion and the bottom portion, the chamber configured to contain the fluid, the chamber in fluid communication with at least one inlet port for receiving the fluid and at least one outlet port for removing the fluid; wherein an optical path of emitted fluorescence from the chamber and an optical path of light emitted by the excitation source do not share a common path to the lens through the chamber.

In some embodiments, the device further comprises: a filter located between the chamber and the lens, the filter for reducing interference between the emitted fluorescence from the fluid and other spectral components.

In some embodiments, the device further comprises at least one additional inlet port and at least one additional outlet port for use in rinsing the chamber.

In some embodiments, the device further comprises a detector for detecting light collected by the lens.

In some embodiments, the detector is a photodetector.

In some embodiments, the detector is a micro-spectrometer.

In some embodiments, the micro-spectrometer comprises a photodetector.

In some embodiments, an optical waveguide is located between the lens and the micro-spectrometer.

In some embodiments, the optical waveguide is an optical fiber.

In some embodiments, the micro-spectrometer is a diffraction grating spectrometer.

In some embodiments, the lens is configured to couple the emitted fluorescence from the fluid into an optical fiber.

In some embodiments, the optical fiber is attached to the lens.

In some embodiments, the top portion includes at least two layers, a first layer comprising the wavelength specific excitation source and a second layer comprising the lens and a detector, wherein the first layer is farther away from the bottom portion than is the second layer.

In some embodiments, the device further comprises a filter located between the chamber and the lens, the filter for reducing interference between the emitted fluorescence from the fluid and other spectral components.

In some embodiments, the detector comprises a micro-spectrometer and a photodetector.

In some embodiments, the micro-spectrometer is monolithically integrated in the second layer.

According to another aspect of the present invention, there is provided a polymer-based microfluidic device for detecting induced fluorescence in a micro-volume of a fluid, the device comprising: a top portion comprising: a wavelength specific light excitation source for inducing fluorescence in the fluid; a detector for detecting emitted fluorescence from the fluid; a bottom portion; a chamber having walls bounded by the top portion and the bottom portion, the chamber configured to contain the fluid, the chamber in fluid communication with at least one inlet port for receiving the fluid and at least one outlet port for removing the fluid; wherein an optical path of emitted fluorescence from the chamber and an optical path of light emitted by the excitation source do not share a common path to the detector through the chamber.

In some embodiments, the device further comprises a filter located between the chamber and the detector, the filter for reducing interference between the emitted fluorescence from the fluid and other spectral components.

In some embodiments, the wavelength specific excitation source is a narrow band source.

In some embodiments, the wavelength specific excitation source is any one of: a wavelength specific light emitting diode (LED); a wavelength specific organic LED (OLED) and a semiconductor laser.

In some embodiments, the narrow band source is a blue wavelength narrow band source.

In some embodiments, the polymer-based device is fabricated from one or more of the following: polydimethylsiloxane (PDMS); photoresist, SU8; poly ethyl acrylate (PEA); poly methyl methacrylate (PMMA); silicon doped PDMS (PsiA); and other derivatives of these materials.

According to yet another aspect of the present invention, there is provided a method for fabricating a polymer-based microfluidic device for detecting induced fluorescence in a micro-volume of a fluid, the method comprising: forming a top portion comprising: integrating in a polymer-based material a wavelength specific excitation source and at least one of: a lens configured to collect fluorescence emitted from the fluid; and a detector; forming a recess in a surface of the top portion that is a partial boundary of a chamber configured to contain the micro-volume of the fluid, the chamber comprising at least one inlet port and at least one outlet port; bonding the surface of the top portion to a bottom portion, the bottom portion forming a remainder of the boundary of the chamber.

In some embodiments, forming the top portion further comprises: integrating a filter in the polymer-based material for reducing interference between the fluorescence emitted from the fluid and other spectral components.

In some embodiments, integrating in the polymer-based material the wavelength specific excitation source comprises: integrating one of: a wavelength specific light emitting diode (LED); a wavelength specific organic LED (OLED) and a semiconductor laser.

In some embodiments, forming the top layer comprises: forming the top portion using a mould that forms the recess in the surface of the top portion.

According to still another aspect of the present invention, there is provided a method for fabricating a polymer-based microfluidic device for detecting induced fluorescence in a micro-volume of a fluid, the method comprising: forming a top portion comprising: integrating in a polymer-based material a wavelength specific excitation source, a lens for collecting emitted fluorescence from the fluid; a detector; a waveguide between the lens and the detector; forming a recess in a surface of the top portion that is a partial boundary of a chamber configured to contain the micro-volume of the fluid, the chamber comprising at least one inlet port and at least one outlet port; bonding the surface of the top portion to a bottom portion, the bottom portion forming a remainder of the boundary of the chamber.

In some embodiments, forming the top portion further comprises: integrating a filter in the polymer-based material for reducing interference between the fluorescence emitted from the fluid and other spectral components.

In some embodiments, forming the top portion comprises forming the top portion in at least two layers, a first layer comprising the wavelength specific excitation source and a second layer comprising the lens and a detector, wherein the first layer is farther away from the bottom portion than is the second layer.

In some embodiments, integrating the detector comprises integrating a micro-spectrometer and a photodetector.

In some embodiments, integrating the micro-spectrometer comprises monolithically integrating a diffraction grating spectrometer.

In some embodiments, forming the top layer comprises: forming the top portion using a mould that forms the recess in the surface of the top portion.

In some embodiments, integrating in the polymer-based material the wavelength specific excitation source comprises: integrating one of: a wavelength specific light emitting diode (LED); a wavelength specific organic LED (OLED) and a semiconductor laser.

According to a further aspect of the present invention, there is provided a microfluidic device for detecting induced fluorescence in a micro-volume of a fluid, the device comprising: a top portion comprising: a wavelength specific excitation source for inducing fluorescence in the fluid; a lens for collecting emitted fluorescence from the fluid; a bottom portion; a chamber having walls bounded by the top portion and the bottom portion, the chamber configured to contain the fluid, the chamber in fluid communication with at least one inlet port for receiving the fluid and at least one outlet port for removing the fluid; wherein an optical path of emitted fluorescence from the chamber and an optical path of light emitted by the excitation source do not share a common path to the lens through the chamber.

In some embodiments, the top portion is fabricated from a polymer-based material and the bottom portion is fabricated from a silicon-based material.

According to still a further aspect of the present invention, there is provided a microfluidic device for detecting induced fluorescence in a micro-volume of a fluid, the device comprising: a top portion comprising: a wavelength specific light excitation source for inducing fluorescence in the fluid; a detector for detecting emitted fluorescence from the fluid; a bottom portion; a chamber having walls bounded by the top portion and the bottom portion, the chamber configured to contain the fluid, the chamber in fluid communication with at least one inlet port for receiving the fluid and at least one outlet port for removing the fluid; wherein an optical path of emitted fluorescence from the chamber and an optical path of light emitted by the excitation source do not share a common path to the detector through the chamber.

In some embodiments, the top portion is fabricated from a polymer-based material and the bottom portion is fabricated from a silicon-based material.

According to another aspect of the present invention, there is provided a method for fabricating a microfluidic device for detecting induced fluorescence in a micro-volume of a fluid, the method comprising: forming a top portion comprising: integrating in a polymer-based material a wavelength specific excitation source and at least one of: a lens configured to collect fluorescence emitted from the fluid; and a detector; forming a recess in a surface of the top portion that is a partial boundary of a chamber configured to contain the micro-volume of the fluid, the chamber comprising at least one inlet port and at least one outlet port; bonding the surface of the top portion to a bottom portion, the bottom portion forming a remainder of the boundary of the chamber.

In some embodiments, bonding the surface of the top portion to a bottom portion comprises bonding the surface of the top portion to a bottom portion that is silicon based.

According to yet another aspect of the present invention, there is provided a method for fabricating a microfluidic device for detecting induced fluorescence in a micro-volume of a fluid, the method comprising: forming a top portion comprising: integrating in a polymer-based material a wavelength specific excitation source, a lens for collecting emitted fluorescence from the fluid; a detector; a waveguide between the lens and the detector; forming a recess in a surface of the top portion that is a partial boundary of a chamber configured to contain the micro-volume of the fluid, the chamber comprising at least one inlet port and at least one outlet port; bonding the surface of the top portion to a bottom portion, the bottom portion forming a remainder of the boundary of the chamber.

In some embodiments, bonding the surface of the top portion to a bottom portion comprises bonding the surface of the top portion to a bottom portion that is silicon based.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the invention will now be described with reference to the attached drawings in which.

DETAILED DESCRIPTION OF THE EMBODIMENTS OF THE INVENTION

Figure 1:
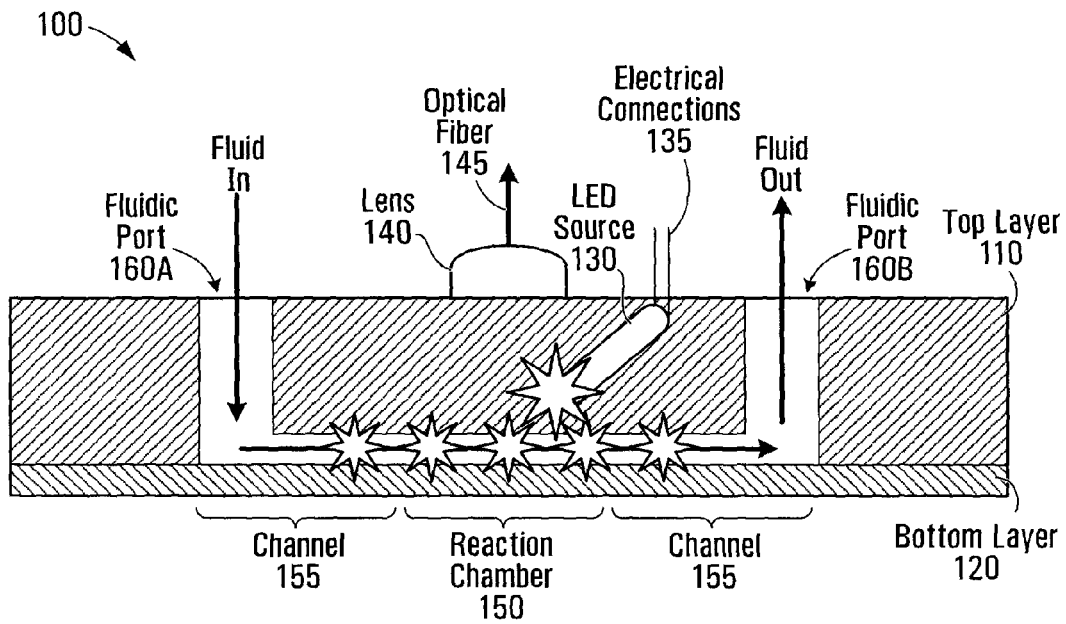
FIG. 1 is a cross sectional view of a microfluidic chip according to a first embodiment of the invention.

The present application is directed to a technological platform with integrated microfluidic and optical modules for bio-detection.

The platform enables in-situ detection by integrating fluidics with optical source and detection capabilities within a fabricated microchip. The platform is a polymer-based or polymer and silicon based microfluidic chip having integrated excitation source and detection elements in a vicinity of a microfluidic reaction chamber configured to contain a micro-volume of a test sample. The principle of detection is based on a bio species, for example antigen, antibodies, cells, enzymes, etc., which is tagged with a marker, such as a quantum dot and/or nano particle that is capable of fluorescing. An excitation source is used to induce fluorescence of the marker within the microfluidic reaction chamber.

In some embodiments, the excitation source is a wavelength specific light emitting diode (LED). LEDs are a suitable excitation source as some types of LEDs have a characteristic of generating a specific wavelength with high luminous intensity at low drive voltages. Some LEDs also have a divergence angle that can be advantageous in illuminating the reaction chamber. For example, a suitable amount of excitation light for a sample within a reaction chamber on the order of a few $mm^2$ can be provided by a wavelength specific LED having a divergence angle of approximately 50°, in close proximity to the reaction chamber.

Using a wavelength specific LED with a narrow bandwidth reduces possible interference with the wavelength of the emitted fluorescence signal from the reaction chamber. This avoids the need for a sharp band pass filter to attenuate light from the excitation source such as would be the case if a broadband source was used as the excitation source. The wavelength specific LED provides a stable excitation source with increased sensitivity.

In some embodiments the excitation source is a narrow band, blue wavelength source.

While a wavelength specific LED is described as an example of an excitation device, it is not intended to limit the scope of the invention. In some embodiments, fluorescent excitation is achieved using a laser source. For example, a semiconductor laser device may be used due to the small size of the device. In some embodiments, fluorescent excitation is achieved using a xenon arc lamp. In some embodiments, fluorescent excitation is achieved using an Organic Light Emitting Diodes (OLED) source.

In some embodiments, the detection elements include one or more of: a lens for collecting emitted fluorescence wavelengths from the reaction chamber, a photodiode and a micro-spectrometer. Examples of a detector using one or more of the detection elements may include, but are not limited to, a lens coupled to an optical fiber where the optical fiber is connected to an external photodiode or spectrometer, a photodiode in close proximity to the reaction chamber, with or without a lens, or a micro-spectrometer including a photodetector integrated in the chip, with or without a lens, and an optical waveguide between the lens and micro-spectrometer. In some embodiments, coupling optics may be used to couple light from the reaction chamber into the waveguide and/or the waveguide into the micro-spectrometer. In some implementations the coupling optics include grin lenses.

The microfluidic chip may have an integrated filter for filtering light from the excitation source before it reaches the reaction chamber or a filter for filtering light after it is emitted from the reaction chamber, but before it reaches the detection elements to reduce spectra that may interfere with the emitted light.

In some embodiments, the excitation wavelength bandwidth of the excitation source is narrowed using an excitation filter so as to provide a source excitation wavelength within required parameters. In a particular implementation, a filter can be monolithically fabricated using a polymer-based material at a location between the excitation source and the reaction chamber to act as a narrow bandwidth filter and allow only a desired wavelength or range of wavelengths to reach the reaction chamber. In some implementations, a discrete filter element of a material other than a polymer-based material is embedded in the chip. In some implementations a polymer-based material is used to monolithically integrate a filter.

In some embodiments, a filter is embedded within the microfluidic chip between the detection elements and the reaction chamber to filter the excitation source wavelengths and other external noise. In some implementations the filter reduces interference with the wavelengths emitted from the reaction chamber and increases sensitivity of the device. In a particular implementation, a filter can be monolithically fabricated using a polymer-based material at a location between the detecting elements and the reaction chamber to act as a narrow bandwidth filter and allow only a desired wavelength or range of wavelengths to reach the detector. In some implementations, a discrete filter element formed of a material other than a polymer-based material is embedded in the chip.

The microfluidic chip may be fabricated using multiple portions of a polymer-based material. A first portion and a second portion are on opposite sides of the microfluidic reaction chamber. For convention purposes, the first portion will be referred to as a top portion and the second portion will be referred to as a bottom portion. In some embodiments, the reaction chamber and channels providing a path for the test sample to reach the chamber may be formed in the top portion. The bottom portion is then bonded to the top portion, forming the reaction chamber for containing the test sample. In some embodiments, the reaction chamber and channels providing a path for the test sample to reach the chamber may be formed in the bottom portion. The top portion is then bonded to the bottom portion, forming the reaction chamber for containing the test sample. In some embodiments, the reaction chamber and channels providing a path for the test sample to reach the chamber may be formed partially in each of the top and bottom portions. The portions are then bonded together, forming the reaction chamber for containing the test sample.

In some embodiments, the top portion has embedded within it the excitation source and detection elements for detecting light emitted from within the reaction chamber. In some embodiments, the top portion has embedded within it the excitation source, and elements for detecting light emitted from within the reaction chamber are bonded to a surface of the top portion opposite to the bottom surface which is bonded to the bottom portion. An example of an element for detection of light is a lens.

In some embodiments, either of the top portion or the bottom portion can be fabricated using a multi-layer process. For example, the top portion may be formed using two layers. In some implementations a first layer of the top portion may be a functional layer, in which a lens, a micro-spectrometer and an optical waveguide from the lens to the micro-spectrometer are monolithically formed, and a photodetector is embedded. In some implementations some or all of the lens, optical waveguide and micro-spectrometer are discrete components embedded in the functional layer. The functional layer is the layer located closest to the bottom portion when the top and bottom portions are bonded together. The excitation source is embedded in a second layer of the top portion formed on top of the functional layer.

In some embodiments, the excitation source and the detection elements are located in the same portion, top or bottom, and are on the same side of the reaction chamber. An optical path of fluorescence emitted from within the reaction chamber in the direction of the detection element and an optical path of light emitted by the excitation source in the direction of the reaction chamber do not share a common path to the detection element through the reaction chamber. In some embodiments, since the optical path of fluorescence to the detection element and the optical path of light emitted by the excitation source to the reaction chamber do not share a common path to the detection element through the reaction chamber, a filter to attenuate light from the excitation source may not be needed. The filter may not be needed as the amount of light received by the detection elements is significantly less than compared to a situation when the source and detector elements are on opposite sides of the reactive chamber share a direct path that includes the reaction chamber.

In some embodiments where a filter is used to reduce interference between the source and light emitted from the fluid in the reaction chamber, the filter can be physically smaller in size than filters that are needed in a situation where the source and detector elements have a direct path that includes the reaction chamber. When the optical path of fluorescence from the reaction chamber and the optical path of light emitted by the excitation source that pass through the reaction chamber do share a common path to the detection elements through the reaction chamber, a filter needs to attenuate a significantly higher intensity from the excitation source since the light emitted by the excitation source is on the same path as the light emitted by the fluid in the chamber.

In some embodiments, positioning of the excitation source and detecting elements in the microfluidic chip can be optimized so as to reduce the amount of light emitted from the excitation source that is directly received by the detecting elements.

When considering suitable material from which to fabricate the microfluidic chip, several factors should be considered. Some of the factors may include, but are not limited to, a) optical, electrical, thermal and mechanical properties of the material, b) ease of working with the material during fabrication, interconnection and packaging, c) permeability of the material and d) biocompatibility of the material with the testing species.

Polydimethylsiloxane (PDMS) is one of the predominantly used materials in fabricating microfluidic devices, especially for biomedical applications. The commercial name of PDMS is Sylgard 184 (Dow Corning Corp.). In some embodiments of the present invention, PDMS is used as a microfluidic device substrate due to its ease of fabrication and integration with excitation source and detection elements to make a hybrid integrated device. Moreover, PDMS is optically transparent in the near UV and visible ranges of the electromagnetic spectrum. The material is both electrically insulating and thermally insulating.

While PDMS is an example of a material that could be used in the fabrication of the device it is not meant to limit the type of materials that could be used. For example, other materials that may be used for fabrication include, but are not limited to, photoresist, SU8, poly ethyl acrylate (PEA), poly methyl methacrylate (PMMA) and silicon doped PDMS (PsiA).

In some implementations, the microfluidic chip is a polymer and silicon based platform. For example, in some embodiments, the top portion is polymer-based and the bottom portion is silicon based. Further examples of such implementations will be described in greater detail below.

Design Implementations

A first example embodiment of a microfluidic chip with an embedded wavelength specific LED source will now be discussed with regard to FIG. 1.

The microfluidic chip 100 consists of an inlet port 160A and at least one rinsing ports (not shown), which intersect and lead to an outlet port 160B. In a particular implementation, not intended to limit the invention, the inlet, outlet 160A, 160B and rinsing ports are 1 mm deep and are each 2 mm in diameter. The inlet, outlet 160A, 160B and rinsing ports are each in fluid connection with a respective channel 155 within the microfluidic chip 100. A region where the channels 155 intersect is a reaction chamber 150. The reaction chamber 150 is a volume within the microfluidic chip 100 that contains a sample under test when the chip is in use. In some embodiments, the reaction chamber 150 is also a center of interest for enzyme interactions and optical detection. In some implementations, the reaction chamber 150 is designed by taking into account the micro-fluidic chip may be reusable. For example, a shape is chosen that avoids corners, which may be difficult to rinse between different samples.

Microfluidic chip 100 includes a top layer 110 and a bottom layer 120. The bottom layer 120 forms a base for the top layer 110. In some embodiments, the reaction chamber 150 is an empty volume between the top layer 110 and the bottom layer 120. As illustrated in FIG. 1, inlet port 160A is an ingress port to provide a test sample to the reaction chamber 150 and outlet port 160B is an egress port to allow the removal of the sample. A wavelength specific LED source 130 is embedded in the top layer 110 in close proximity to the reaction chamber 150. Electrical connections 135 for LED 130 are exposed outside of the top layer 110. The electrical connections 135 can be connected to a power supply to power LED 130. A lens 140 is bonded on a top surface of the top layer 110. An optical fiber 145 is coupled to the lens.

In operation, a sample in the form of a fluid containing tagged markers is introduced via the inlet port 160A into the channel 155 and fills the reaction chamber 150. In some embodiments, the tagged markers may include one or more of, but not limited to, the following types of tagged markers: fluorophores; quantum dots; dyes; and nano particles. Light from the powered LED 130 excites the tagged markers of the sample in the reaction chamber 150 and causes the markers to fluoresce. The fluorescence emitted in a direction toward a top surface of the top layer 110 is collected by the lens 140 and is coupled into the optical fiber 145. The optical fiber 145 is coupled to a measurement recording device to provide an indication of the amount of fluorescence in the sample. In some implementations, the measurement recording device may include a spectrometer and/or other measurement recording software/hardware and/or a display.

Figure 2:
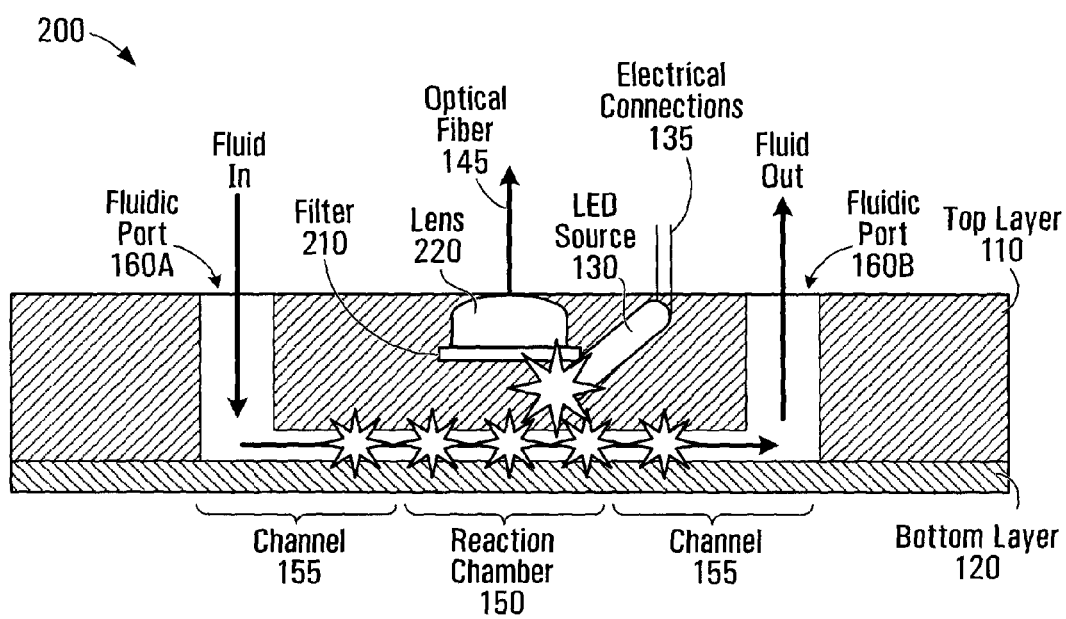
FIG. 2 is a cross sectional view of a microfluidic chip according to a second embodiment of the invention.

A second example embodiment of a microfluidic chip with an embedded wavelength specific LED source, light collecting lens and optical fiber will now be discussed with regard to FIG. 2. Microfluidic chip 200 illustrated in FIG. 2 is similar to the microfluidic chip 100 of FIG. 1 in several respects. Microfluidic chip 200 includes a top layer 110 and a bottom layer 120. The reaction chamber 150 is located between the top layer 110 and the bottom layer 120. Inlet and outlet ports 160A, 160B and channels 155 are passages through the top layer 110 in fluid communication with the reaction chamber 150. The wavelength specific LED source 130 is embedded in the top layer 110 in close proximity to the reaction chamber 150.

With regard to detecting fluorescence emitted from tagged markers of the sample in the reaction chamber 150, a lens 220 and an optical fiber 225 are embedded in the top layer 110 in close proximity to the reaction chamber 150. In some embodiments, a diverging lens is used to collect the emitted fluorescence. In some embodiments, the lens and optical fiber are discrete components that are coupled together during the fabricating process. In other embodiments, the lens and optical fiber are an integrated component before embedding the component into the microfluidic chip 200.

In the illustrated embodiment, a filter 210 is also embedded in the top layer 110 between the reaction chamber 150 and the lens 220. The filter 210 is used to block wavelengths of excitation signal from the LED 130 and scattered light that may interfere with the fluorescence emitted from the reaction chamber 150. While a filter may be advantageous in some implementations, for example to improve the sensitivity of the device, other implementations may not include such a filter.

Operation of the second embodiment is substantially the same as the first embodiment.

In some implementations embedding the fiber 145 and lens 220 within the microfluidic chip 200 may allow repetitive sets of measurements to be achieved in a more consistent manner.

A third example embodiment of a microfluidic chip with an embedded wavelength specific LED source will now be discussed with regard to FIG. 3. In the illustrated embodiment of FIG. 3, several of the elements are substantially the same as those in FIGS. 1 and 2. For example, microfluidic chip 300 includes the top layer 110, the bottom layer 120, the wavelength specific LED source 130, the reaction chamber 150, and inlet, outlet 160A, 160B and rinsing ports. However, in the example of FIG. 3, instead of using a lens and optical fiber to collect fluorescence emitted from the microfluidic chamber 150, a photodetector 320 is embedded in the top layer 110 in close proximity to the reaction chamber 150. The photodetector 320 has electrical connections 325 extending out of the top layer 110 to power the photodetector 320, if it is an active component, and to provide the electrical signal representing the received optical fluorescence to a measurement recording device and/or a display.

Figure 3:
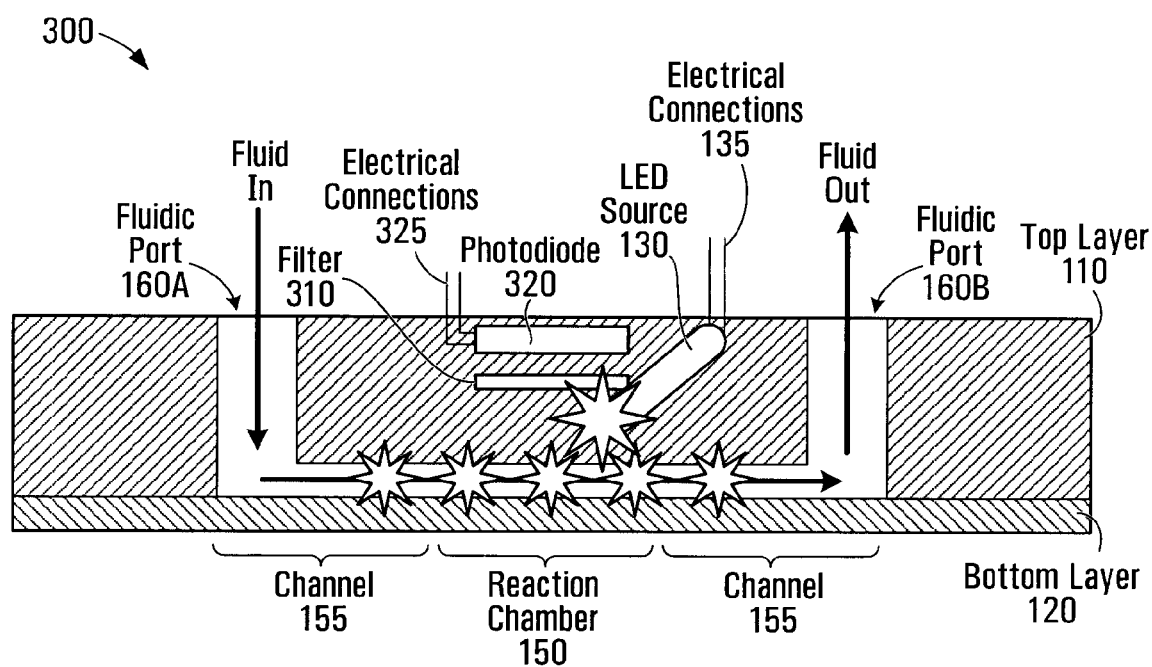
FIG. 3 is a cross sectional view of a microfluidic chip according to a third embodiment of the invention.

In some other embodiments, there are optical elements, such as, for example, a filter, and/or one or more lens between the detector and microfluidic chamber for efficient light collection (not shown in FIG. 3).

The embodiment illustrated in FIG. 3 includes a high transmission cut off filter 310 embedded in the top layer 110 between the reaction chamber 150 and the photodetector 320. The filter 310 is used to block wavelengths of the excitation signal and scattered light that may interfere with the output signal. While the filter may be advantageous in some implementations, for example to improve the sensitivity of the device, other implementations may not include such a filter.

In some embodiments, the photodetector 320 is a wavelength specific photodetector.

A photodetector integrated into the microfluidic chip may make the microfluidic chip 300 simpler and easier to handle as compared to the two previously described embodiments. Those embodiments generate an optical signal that is converted to an electrical signal external to the device. Any loses in the optical signal along the path prior to the conversion to an electrical signal may negatively affect the resulting measurement. The present embodiment converts the optical signal to an electrical signal substantially at the point of measurement. In some embodiments, the embedded photodiode may improve robustness and sensitivity of testing performed by the microfluidic chip 300.

Figure 4A:
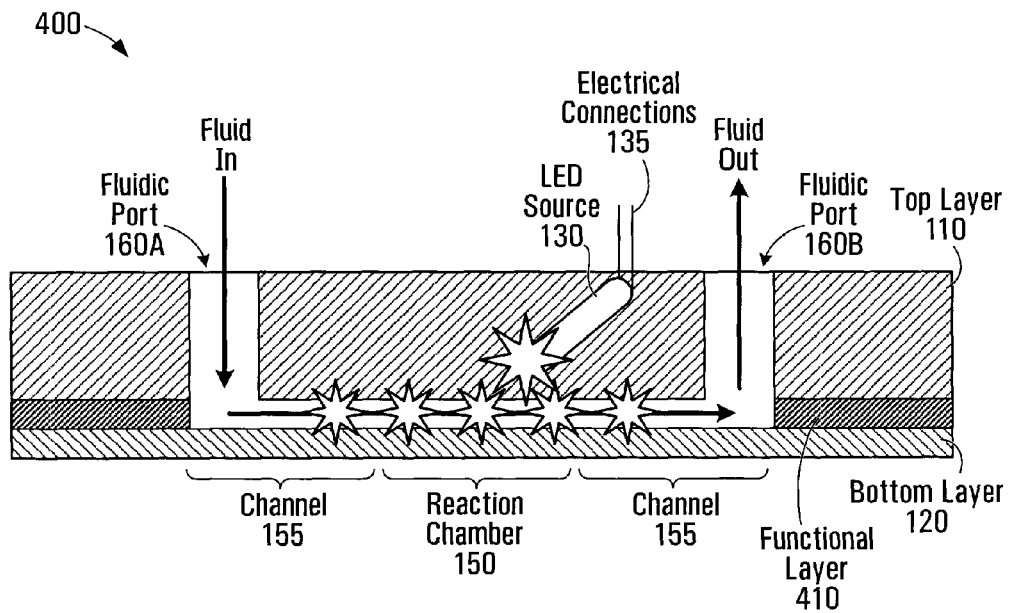
FIG. 4A is a cross sectional view of a microfluidic chip according to a fourth embodiment of the invention.
Figure 4B:
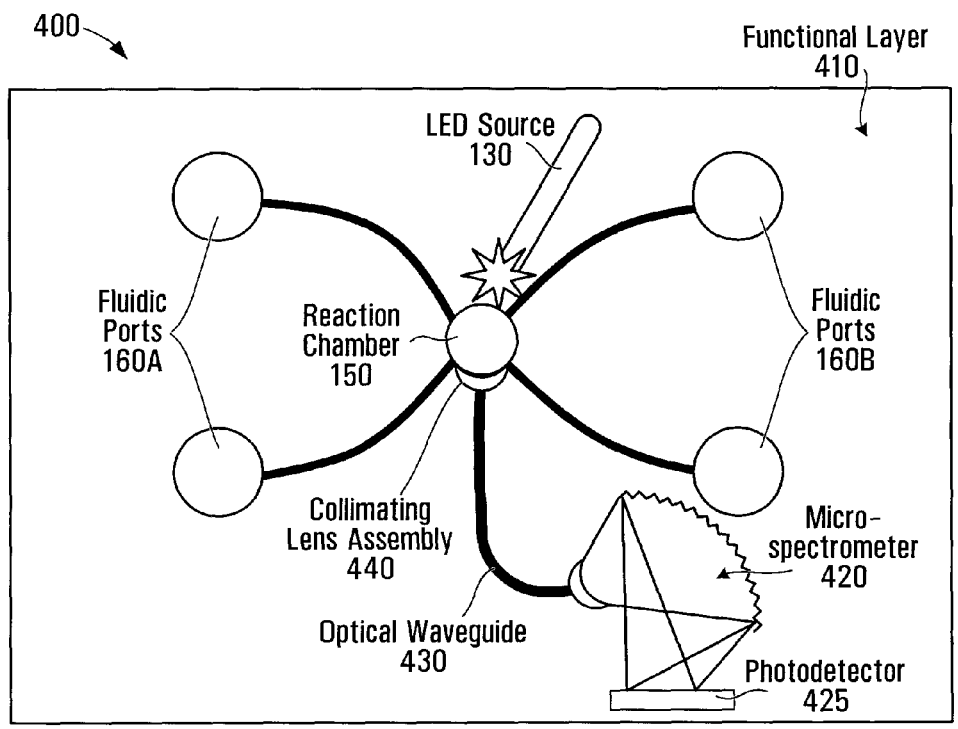
FIG. 4B is a top view of a microfluidic chip shown in FIG. 4A.

A fourth example embodiment of a microfluidic chip with an embedded wavelength specific LED source will now be discussed with regard to FIG. 4A and FIG. 4B. In the illustrated embodiment of FIG. 4A and FIG. 4B, several of the elements are substantially the same as those in FIGS. 1 and 2. For example, microfluidic chip 400 includes the top layer 110, the bottom layer 120, the wavelength specific LED source 130, the reaction chamber 150, and inlet, outlet 160A, 160B and rinsing ports.

Microfluidic chip 400 includes a third polymer layer, a functional layer 410, located between the bottom layer 120 and top layer 110. In some implementations, the functional layer 410 is substantially the same thickness as the reaction chamber 150. However, in other implementations, the functional layer 410 has a thickness that is greater than or less than the reaction chamber 150. The functional layer 410 includes a fabricated integrated micro-spectrometer 420, as indicated in FIG. 4B. A collimating lens assembly 440 is located in the functional layer 410 in close proximity to the reaction chamber 150 to collect fluorescence emitted by the test sample that is illuminated in the reaction chamber. In some embodiments, the collimating lens assembly 440 includes a filter to attenuate spectral components that may interfere with the fluorescence emitted from the sample. While a filter may be advantageous in some implementations, for example to improve the sensitivity of the device, other implementations may not include such a filter. As discussed above, the top layer 110 and the functional layer 410 together may be considered as a multilayer top portion of the microfluidic chip 400 and the bottom layer may be considered a bottom portion of the microfluidic chip 400.

An optical waveguide 430 is located between the collimating lens assembly 440 and the micro-spectrometer 420. In some embodiments the optical waveguide 430 is an optical fiber embedded in the functional layer 410. In some embodiments the optical waveguide 430 is a material with a different index of refraction than the rest of the functional layer 410. In some embodiments, the multiple layers of the device could be different polymer materials having different optical properties to achieve optical propagation in the functional layer 410.

In some embodiments, a photodetector 425 is embedded in the functional layer 410 in close proximity to the micro-spectrometer 420 at a location allowing diffracted light from the micro-spectrometer 420 to be detected. In some embodiments, the fabrication of microfluidic chip 400 is achieved by monolithically integrating micro-moulded gratings and embedding a photodetector assembly in the functional layer 410. In other embodiments, the photodetector is externally attached.

In operation, the powered LED source 130 causes the test sample in the reaction chamber 150 to fluoresce. Fluorescence emitted from the reaction chamber 150 in the direction of the collimating lens assembly 440 is collected by the collimating lens assembly 440. The collimated light propagates through the optical waveguide 430 to the micro-spectrometer 420. The fluorescence light is diffracted by gratings of the micro-spectrometer 420 and is detected by the photodetector 425. The output of the photodetector 425 is provided to a measurement recording device and/or a display.

In some implementations, functionality is incorporated into the microfluidic chip to enable the channels and reaction chamber to be rinsed out.

In some embodiments, size matching of reaction chamber geometry with the detection elements provides improved signal detection capability and sensitivity.

In some embodiments, circuits and electronic chips for applications involving enzyme transduction, separation, counting and imaging of flowing samples may be integrated into the microfluidic chip.

In some embodiments, performance and functionality in terms of measurement resolution, sensitivity and repeatability is improved by an ability to incorporate the excitation source and detection elements in close proximity within the microfluidic chip.

In some embodiments, a minimum detectable limit of fluorescence is improved due to the close proximity of the excitation source and the detection elements with the reaction chamber.

In the embodiments described above, the channels and reaction chamber are described as formed in the top layer, but this is not intended to limit the device to this specific implementation. In other implementations, the channels could be formed in the bottom layer, or partially in the top layer and partially in the bottom layer.

Fabrication of the Polymer-Based Microfluidic Chip

Soft lithography has emerged as a popular fabrication technique for microfluidic devices. It is a simple, effective and inexpensive fabrication technique that uses a polymer in a replica moulding type process. The technique does not need a clean room facility for fabrication.

However, fabrication of the described microfluidic chips is not intended to be limited to this process and other processes are contemplated. Some other possible fabrication methods may include, but are not limited to, Nanoimprint lithography, embossing, bonding and lithography on polymers.

In some implementations of fabricating the top PDMS layer, fabrication is based on two-layer soft lithography technique. Such a process may be used in fabricating microfluidic chips according to the first three example embodiments described above. In some embodiments, a three-layer soft lithography technique is used in fabrication. Such a process may be used in fabricating microfluidic chips according to the fourth example embodiment described above. The two and three-layer soft lithography techniques allow integrating of the LED source, excitation and/or emission filters, if desired, and detection elements, such as lenses, photodetectors and/or micro-spectrometers, within the microfluidic chip.

Figure 5A:
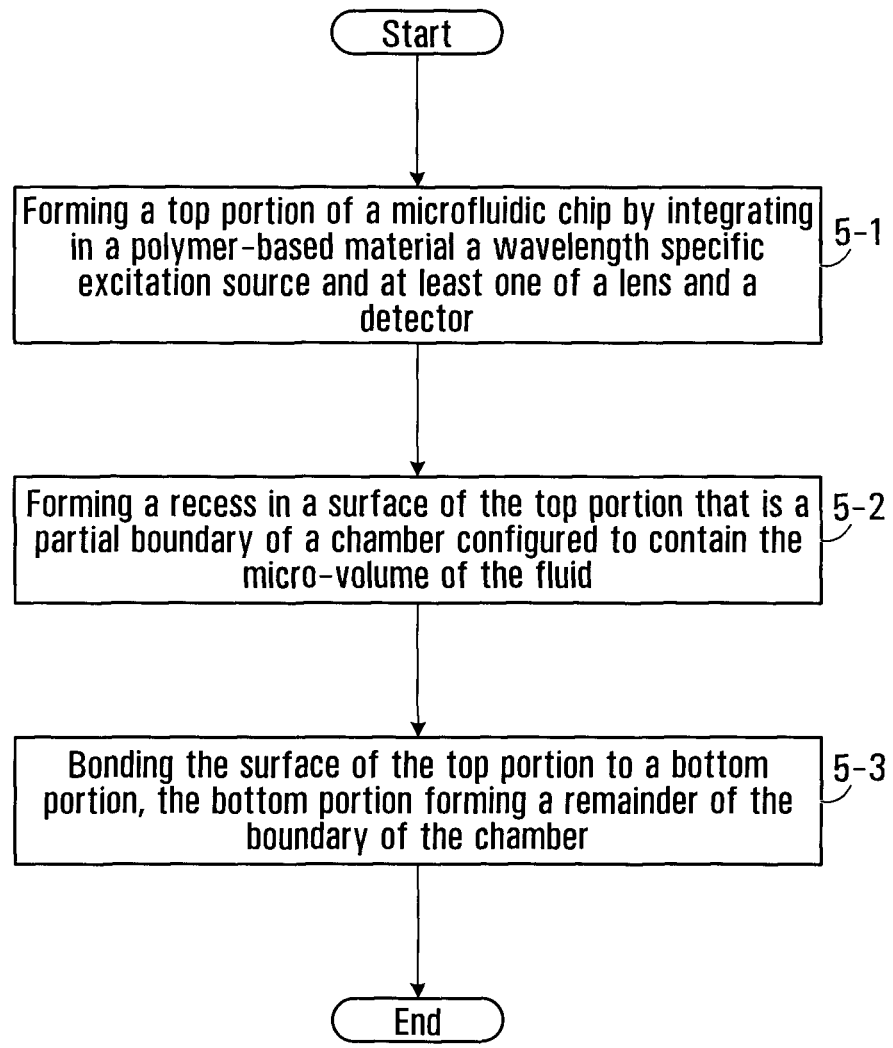
FIG. 5A is a flow chart for a method of fabricating a microfluidic chip according to an embodiment of the invention.
Figure 5B:
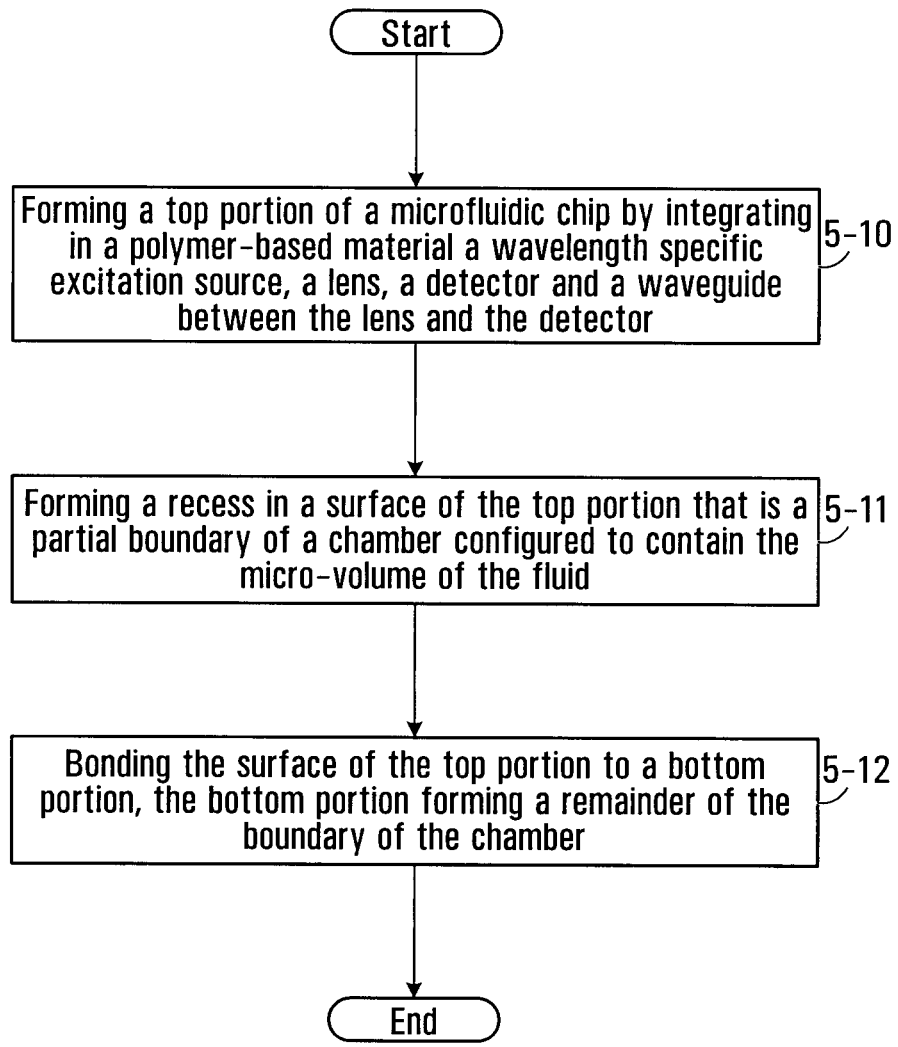
FIG. 5B is a flow chart for a method of fabricating a microfluidic chip according to another embodiment of the invention.

With reference to FIGS. 5A and 5B, general methods for fabricating a microfluidic chip will now be described. The fabrication methods include forming a top portion of the chip and bonding the top portion to a bottom portion. Forming the top portion involves embedding discrete source components and detection elements in a polymer-based material that forms the top portion. The detection elements may be discrete components and/or monolithically integrated in the polymer-based material. The bottom surface of the top portion has recesses that, in part, form channels and a reaction chamber. Once the bottom portion is bonded to the top portion, the channel and reaction chamber recesses form sealed conduits, accessible by inlet and outlet ports, and a reservoir to receive a test sample.

In some implementations of fabricating the device, a preliminary step involves forming a master template consisting of a positive impression of a pattern used to create the top portion of the microfluidic chip. The positive impression for example forms the recesses of the channels and reaction chamber in the bottom surface of the top layer. In some embodiments, the master template is created using micromachining techniques on silicon or other materials.

In FIG. 5A, fabricating the microfluidic chip involves forming the top portion. Forming the top portion involves several steps. A first step 5-1 of forming a top portion involves integrating in a polymer-based material a wavelength specific LED and at least one of a) a lens configured to collect fluorescence emitted from the fluid and b) a detector. In some embodiments, a filter for reducing interference between the emitted fluorescence from the sample and other spectral components may also be integrated in the top portion. A second step 5-2 of forming a top portion involves forming a recess in a surface of the top portion that is a partial boundary of a chamber configured to contain a micro-volume of the fluid that is the test sample, the chamber comprising at least one inlet port and at least one outlet port. The steps may be performed simultaneously, in the sequence described, or in a reverse of the described sequence.

A subsequent step 5-3 of fabricating the microfluidic chip involves bonding the surface of the top portion to a bottom portion, the bottom portion forming a remainder of the boundary of the chamber.

In some embodiments, such a method of fabricating a microfluidic chip may be used for fabricating chips similar to the first, second and third microfluidic chip example embodiments described above. A more detailed example of a fabrication process will be described below.

In FIG. 5B, fabricating the microfluidic chip involves forming a top portion of the device. Forming the top portion involves several steps. A first step 5-10 of forming a top portion involves integrating in a polymer-based material a wavelength specific LED, a lens for collecting emitted fluorescence from the fluid; a detector; and a waveguide between the lens and the detector. In some embodiments, a filter for reducing interference between the emitted fluorescence from the sample and other spectral components may also be integrated in the top portion. In some embodiments, integrating the detector in the top portion involves monolithically integrating a spectrometer in the top portion. In some embodiments, components integrated in the top portion are discrete components. A second step 5-11 of forming a top portion involves forming a recess in a surface of the top portion that is a partial boundary of a chamber configured to contain the micro-volume of the fluid that is the test sample, the chamber comprising at least one inlet port and at least one outlet port. The steps may be performed simultaneously, in the sequence described, or in a reverse of the described sequence.

A third step 5-12 of fabricating the microfluidic chip involves bonding the surface of the top portion to a bottom portion, the bottom portion forming a remainder of the boundary of the chamber.

In some embodiments, the lens, the detector and the waveguide between the lens and the detector are integrated in a first layer of the top portion and the LED is integrated in a second layer, wherein the second layer is farther away from the bottom portion than is the second layer.

In some embodiments, such a method of fabricating a microfluidic chip may be used for fabricating chips similar to the fourth microfluidic chip embodiment described above.

A particular example of a process for fabricating a microfluidic chip according to the first embodiment described above is described below with reference to FIGS. 6 to 12. The specific details of the example, such as dimensions used in creating the mould template, volumes of polymer mixed to form each layer of the top and bottom portions at each given step, sizes of the o-rings/washers used in the chip, manner of curing the polymer (temperatures, durations, etc.), the type of material used for tubes at the inlet, outlet and rinsing ports, a process for creating the bottom portion of the chip, process of cleaning and bonding the top and bottom layers, including the particular type of bonding medium used, are illustrative in nature and are not meant to limit the invention.

Figure 6:
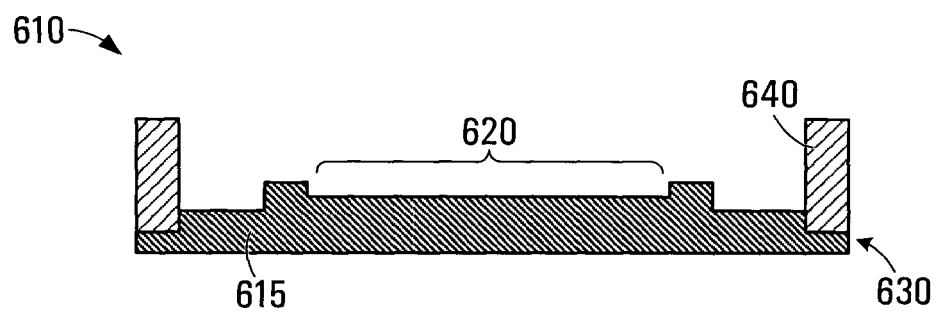
FIG. 6 is a cross sectional view of a master mould template for fabricating a top portion of a microfluidic chip according to an embodiment of the invention.

Step 1: Firstly, a master template mould consisting of a positive impression of a pattern that forms the top portion of the chip including channels and the reaction chamber is fabricated using a micromachining or a conventional machining technique. The master could be made from silicon, plastic, metal or any other suitable material. The master is then used as a mould to cast the top portion. FIG. 6 illustrates a cross sectional view of the master template mould 610 including a fixture 615 having channel and microfluidic chamber patterns 620 and a square ring 640 on the edge of the fixture. The channel and chamber patterns 620 are surrounded by a 3 mm deep square slot 630. A 7 mm high square ring 640 fits into the slot 630 and forms a closed wall around the perimeter of the fixture. Designing the template as an assembly of fixture and square ring may reduce fabrication time and cost of machining the mould. In other implementations the mould may be machined from a single piece of material.

In some implementations, the parts forming the mould are prepared from brass metal and are gold plated to reduce the surface roughness of the template. This may enhance the non-sticking property of the surface and ease removal of cured elastomer from the template. Thus, a surface treatment or silanisation of the mould template is not necessary to facilitate de-moulding.

In some implementations, the mould may be micromachined from silicon or other materials. In some implementations, the surface could be silanized or made hydrophilic enough for the removal of polymer.

Step 2: A petri dish is placed on a digital balance and an exact amount of 6 gms of pre-polymer is poured onto the petri dish using a 1 ml syringe. One-tenth the ratio of curing agent is then poured to the petri dish using a disposable plastic pipette and the mixture is properly mixed for an appropriate time interval to ensure complete mixing between the two parts. The mixture is a highly viscous pre-polymer fluid at room temperature. It is then placed in a desiccator/vacuum pump until all the trapped air bubbles escape from the pre-polymer.

Figure 7:
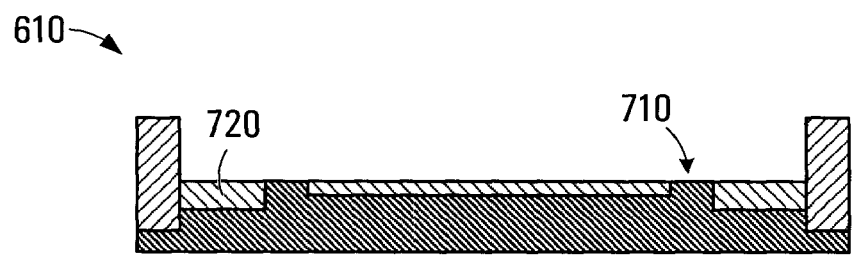
FIG. 7 is a cross sectional view of the master mould template of FIG. 6 in which a polymer has been added to form a first polymer layer.

The mixture is poured into the template mould 610 as shown in FIG. 7 using a plastic pipette up to the brim of the template ports 710 to form a first layer 720. For example this may be to a height of approximately 1 mm. The template mould 610 is put inside a curing oven and the polymer is cured for 60 minutes at 75° C. The oven is connected to high/low limit over temperature controller to provide reliable control of temperature within the equipment.

The pre-polymer conforms to the shape of the template mould 610 and replicates the features of the mould. The curing agent contains silicon hydride groups, which reacts with the vinyl groups in the pre-polymer and initiates polymerization chain reaction to make a solid mass. The polymerized layer consists of microchannels, chamber and fluidic ports.

Figure 8:
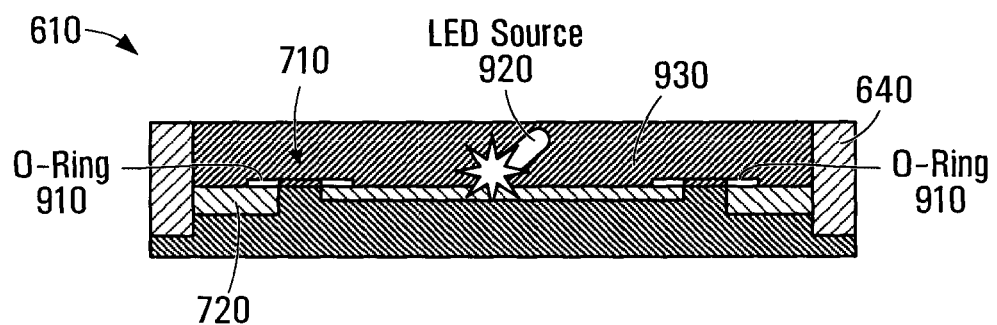
FIG. 8 is a cross sectional view of the master mould template of FIG. 6 in which washers/o-rings are located at positions of the ports and an LED is located within the top portion.

Step 3: After the first layer 720 has at least partially cured, washers/o-rings 910 are placed at the top of each of the locations of where the ports 710 will be located in the final chip, as shown in FIG. 8. The washers/o-rings 910 provide transverse strength to the holes forming the port locations and aid in maintaining the position of tubes that will form the ports. In the illustrated implementation the washers/o-rings 910 are made up of 500 µm thick polycarbonate (PC) material. The washers/o-rings are prepared by using a piercing and blanking punch. An inner diameter of the washer/o-ring is measured to be 1.8 mm and the outer diameter as 7 mm. The inner diameter of the rings form a clearance fit with portions of the template mould 610 representing the locations of the fluidic ports 710.

A wavelength specific LED 920 is placed at the top of the first layer above the reaction chamber as shown in FIG. 8, such that the tip of the LED 920 is pointing to the base of the reaction chamber at the intersection of the channels. Electrical connections (not shown) of the LED 920 are left exposed above the wall 640 of the template mould 610. The temperature used to cure further layers added to the microfluidic chip should not exceed the specified storing range of the LED 920.

Additional uncured pre-polymer is poured into the template to embed the LED 920 within the top portion, forming a second layer 930. The template mould 610 is placed inside the oven and the polymer is cured for another 60 minutes at 75° C. The partially cured first layer 720 of the top portion bonds to the second layer 930 to make an integrated piece of polymer with the LED 920 and o-rings 910 embedded within it.

Figure 9:
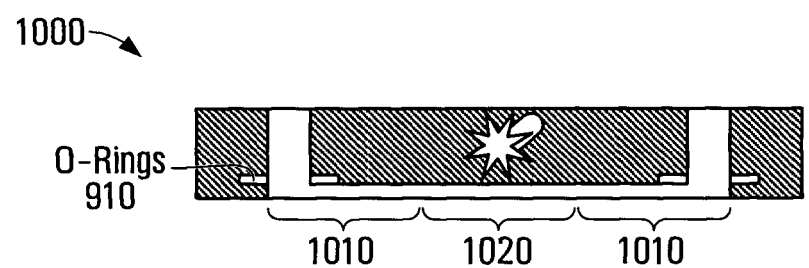
FIG. 9 is a cross sectional view of a cured polymer chip that is removed from the master template and forms a top portion of the microfluidic chip.

Step 4: The cured polymer microfluidic chip is gently removed from the template mould. This forms the top portion 1000 of the microfluidic chip consisting of recesses for channels 1010 and the reaction chamber 1020 as seen in FIG. 9. Through holes at the location of the o-rings/washers 910 are punched through the top portion using a 2 mm diameter hole-punch tool to form the four fluidic ports that are the inlet, outlet and rinsing ports.

Figure 10:
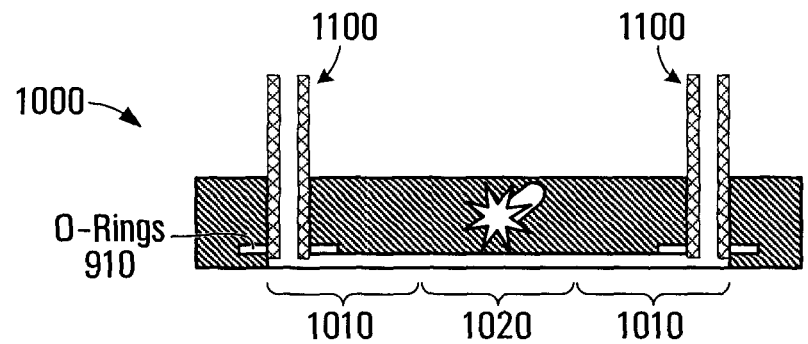
FIG. 10 is a cross sectional view of the top portion of the microfluidic chip with PVC tubes inserted.

Step 5: The next step is to connect the microfluidic chamber to the external world using tubes. FIG. 10 illustrates a cross sectional view of the top portion 1000 with tubes 1100 inserted into the punched holes that form the fluidic ports. In the illustrated implementation, the tubes are PVC tubes, one for each fluidic port, approximately 7 cm in length and having an outer diameter of 2.2 mm and inner diameter of 0.25 mm are pushed from the top surface of the top portion 1000 and gently pulled through each of the holes. Care must be taken while inserting the tubes 1100 into the chip through the o-rings 910 as lack of care handling the tubes may damage the polymer. One technique for inserting a tube into the o-ring 910 is to first cut the end of the tube at an angle of 10°-15° with reference to the longitudinal axis of the tube, resulting in approximately the last centimeter of the tube being angled. The angled end is inserted from the top surface and gently pulled through the hole from the bottom surface. The angled end portion of the tube is then removed. The tubes 1100 each form an interference fit with the respective fluidic port o-ring Subsequent to removing the angled end portion of the tubes, the end of each tube is withdrawn within the bottom surface of the top portion 1000. If the tubes 1100 are left to overhang the bottom surface, the overhanging portion may interfere with a bottom portion when the top portion and the bottom portion are bonded together. Also, if the gap between the tube exit and the bottom portion forming a bottom channel wall is too small, this may create fluid shear forces in Non-Newtonian fluids.

Figure 11:
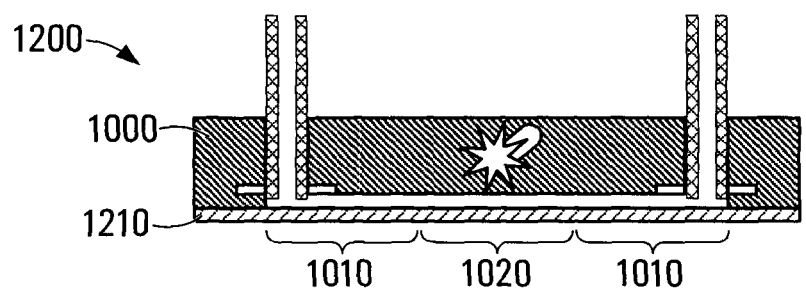
FIG. 11 is a cross sectional view of the top portion of a microfluidic chip attached with a bottom portion.

Step 6: In this step, a bottom portion having a flat surface is bonded to the bottom surface of the top portion 1000 having the reaction chamber 1020 and channel 1010 recesses in order to form the microfluidic chip with a sealed reaction chamber accessible via the fluidic ports and channels. FIG. 11 shows the microfluidic chip 1200 having top 1000 and bottom 1210 portions bonded together.

In some embodiments, a bottom portion 1210 is bonded to the bottom surface of the top portion 1000 by bonding the top portion 1000 to a thin polymer sheet using a polymer adhesive. PDMS and similar siloxane polymers have a relatively low curing temperature, thus they are the most common adhesive bonding materials for microfluidic devices.

In one fabrication implementation, a 100 µm thick flat polymer sheet is prepared by using a smooth and flat steel template. Polymerized PDMS is peeled off the flat template and cut into a 28×28 mm sheet. A silicone adhesive, for example "SE 9186 clear" (Dow Corning Corporation) is used as a bonding agent to irreversibly bond the top portion of the microfluidic chip to the bottom sheet.

To increase the surface area for bonding, in some implementations the surfaces of the top and bottom portions may be filed and abraded. This may be performed for example by using a high flat needle hand-file. The top and bottom portions may then be cleaned in a stream of compressed nitrogen to remove abraded PDMS particles and cleaned with water.

Before bonding, the top and bottom portions are thoroughly cleaned first using acetone or isopropyl alcohol (IPA) to remove any dust and/or oil layer. The parts may also be subsequently cleaned with diluted HCl (HCl:DI=1:5) for 10 minutes to enhance its surface property. The parts then may be dried in a stream of compressed nitrogen. Exposure to nitrogen gas also removes moisture content and dust particles.

A very thin and uniform layer of adhesive is applied on the abraded surface of the bottom portion 1210. The thin layer of adhesive on the bottom portion 1210 should be sufficient to bond both the top portion 1000 and the bottom portion 1210 together. Therefore, in some implementations additional adhesive does not have to be applied to the bottom surface of the top portion. The top 1000 and bottom 1210 portions are then placed in contact with each other and held together with a gentle compressive force.

Step 7: In a further step, a lens may be bonded to the top surface of the top layer of the microfluidic chip.

In some implementations, the microfluidic chip can be included in a package. In some implementations such a package may be similar to standard integrated circuit (IC) type packages. Therefore, connection of electrical requirements, such as powering of the excitation source and/or powering of a detector, could be performed by connecting to connectors or pins on the package.

In some embodiments, instead of a purely polymer based platform for the top and bottom layers of the microfluidic device, the microfluidic device is fabricated using a combination of silicon and polymer platforms.

In a particular example, the bottom layer is made of silicon in which partial or complete microfluidic channels and/or reaction chamber can be etched using for example anisotropic micromachining methods like TMAH (tetral methyl ammonimum hydroxide) etching, DRIE (deep reactive ion etching), plasma etching, RIE (reactive ion etching), chemical etching or isotropic micromachining methods such as $XeF_2$ (Xenon di fluoride) gas phase micromachining. A "partial" channel or chamber is intended to, in combination with a partial channel and/or chamber in the top polymer layer, form a complete channel and/or chamber. A complete channel and/or chamber in the bottom silicon layer is intended to be the complete channel and/or chamber formed in the bottom silicon layer, with no portion of the channel/chamber formed in the top polymer layer.

The top layer is polymer based and may or may not have complementary microfluidic channels and reaction chamber. The top layer could have one or more of the source and detection elements, for example, LED source, lens, filters and photodiode, as well as the fluidic ports. The top layer can be bonded with the silicon based bottom layer to form the microfluidic device.

In another example, the silicon bottom chip is replaced with SOI (silicon on insulator) material. In a particular example implementation, an SOI wafer includes a handle silicon layer and an active silicon layer, with a buffer oxide (BOX) layer sandwiched between them. The top surface of the bottom silicon layer, that is the surface that comes into contact with the bottom surface of the top polymer layer, is the active silicon layer. The active silicon layer thickness can be from sub micron to hundreds of microns thick. The handle layer is on the bottom surface of the bottom silicon layer. Partial or complete microfluidic channels and/or reaction chamber can be etched in the active silicon layer using anisotropic micromachining methods like TMAH etching, DRIE (deep reactive ion etching), plasma etching, RIE (reactive ion etching), chemical etching or isotropic micromachining methods such as $XeF_2$ gas phase micromachining. In addition, in some implementations, such as for example implementations similar to FIGS. 4A and 4B, one or more optical elements, such as the waveguide, the micro-spectrometer, and/or optical coupling elements, can also be fabricated in the active silicon layer using the silicon fabrication methods.

The top layer is polymer based and may or may not have complementary microfluidic channels and reaction chamber. The top layer could have one or more of the source and detection elements, for example, LED source, lens, filters and photodiode, as well as the fluidic ports. The top layer can be bonded with the silicon based bottom layer.

Figure 12:
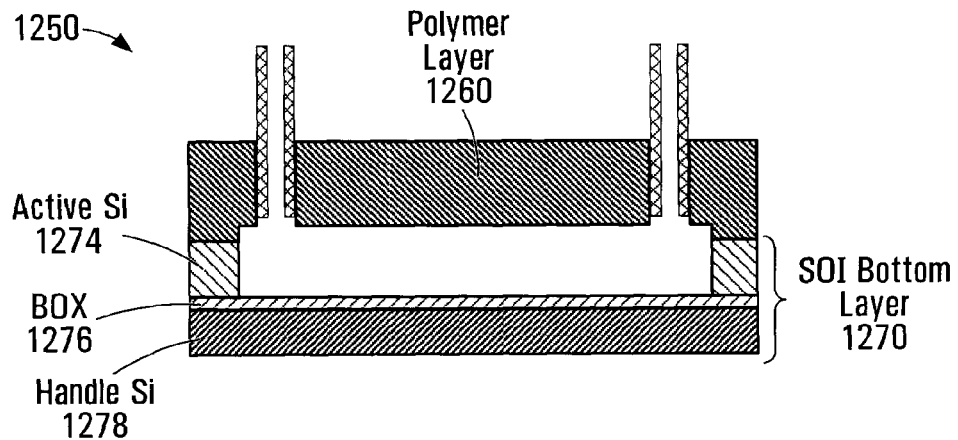
FIG. 12 is a cross sectional view of a microfluidic chip according to a further embodiment of the invention

FIG. 12 illustrates an example of a polymer and silicon based microfluidic device 1250 without any of the optical source and detection elements being shown in the figure. In some implementations, the optical source and detection elements can be arranged in similar fashion to any one of FIGS. 1 to 3, 4B and 4B.

In FIG. 12 the polymer and silicon based microfluidic device 1250 includes a top layer that is a polymer layer 1260. A silicon based bottom layer 1270 bonded to the polymer top layer 1260 includes a handle silicon (Si) layer 1278 and an active silicon (Si) layer 1274, with a buffer oxide (BOX) layer 1276 sandwiched between the active and handle Si layers 1274, 1278.

In embodiments in which the bottom layer is fabricated from silicon or SOI, the bottom layer is micromachined with anisotropic or isotropic silicon micromachining methods. In this step, any combination of elements, namely, microfluidic channels, reaction chambers, waveguides, micro-spectrometer, and/or optical coupling elements can be formed in full or in part.

Similar fabrication processes can be used to fabricate chips of other designs, as described above. For fabrication of a chip in which a lens and fiber are integrated in the top portion, in step 4 of the process described above, the lens and fiber are embedded in the second layer of the polymer at the same time as LED. In another implementation, the LED is embedded in the second layer, but the second layer does not fill the template mould to the top. Adequate room is left for a third layer to be added. After the second layer has been cured, the lens and fiber are placed on the top of the second layer and the third layer of polymer is added. In either of these implementations, one or more filters may be included between the reaction chamber and the lens. The first, second and third layers may be the same polymer mixture, or may be different polymer mixtures.

For fabrication of a chip that includes a detector, the detector may be embedded in the second layer at the same time as the LED in similar fashion to step 4. In another implementation, the second layer does not fill the template mould to the top, leaving room for a third layer to be added. After the second layer has been cured, the detector is placed on the top of the second layer and the third layer of polymer is added. In either of these implementations, one or more filters may be included between the reaction chamber and the lens. The first, second and third layers may be the same polymer mixture, or may be different polymer mixtures.

For fabrication of a chip that includes an integrated microspectrometer, collimating lens assembly, optical waveguide, spectrometer and photodetector, these elements are integrated in a second layer and the second layer of polymer is not filled to the top of the template mould in similar fashion to step 4. The elements may be a mix of discrete components and/or elements that are monolithically integrated in the chip. After the second layer has been cured, the LED is placed on the top of the second layer and a third layer of polymer is added. The first, second and third layers may be the same polymer mixture, or may be different polymer mixtures.

Testing the Micro-Fluidic Chip

The following section describes a particular example test setup employed for testing the microfluidic chip. A hydrophilic nature of the fabricated microfluidic chip is retained by sealing and enclosing the chamber and channels in a film of distilled or deionized (D.I.) water.

The microfluidic chip is mounted on a micro-positioner so that the position of the chip is adjustable with respect to an optical fiber, into which light from the lens is coupled. An integrated bio-sensing system is set up by coupling light from the chip to a 250 μm core diameter SMA fiber. The system is constructed in such a way that the core of the fiber is aligned with the lens in such a way to maximize the optical output from the lens. The other end of the fiber is connected to a detecting device, for example an Ocean Optics USB2000 Plug-and-Play Spectrometer to allow measurements to be made and/or recorded.

The output signal is detected with Ocean Optics OOI-Base32 Spectrometer Operating Software interfaced to a computer. Peak detected signal, normalized fluorescence, relative fluorescence and minimum detectable concentration of the sample needed for detection is determined using spectrometer's OOIBase32 software and tabulated with spreadsheets using standard procedures.

Stability of LED Emission at Different Voltages

The stability of the LED source for a specific time interval can be determined in order to determine an appropriate and consistent input voltage to the microfluidic chip. A precise and constant DC supply voltage is used to excite the LED source such that the source emits a stable light intensity for a prolonged duration without compromising the sensitivity of the sensor.

Bio-Optical Testing on Microfluidic Chip

Selection and Preparation of Enzymes

To demonstrate a practical application, limit of sensitivity on inlet and rinsing flow conditions, and to compare the performance of LED induced microfluidic chip, LED induced fluorescence tests have been performed for different concentrations of antigen. A vial of donkey anti-sheep IgG conjugates (Invitrogen—Molecular Probes, Canada) was tested. The sample was a 2 mg/mL solution in 0.1 M sodium phosphate, 0.1 M NaCl, pH 7.5, containing 2-5 mM sodium azide and tagged to Alexafluor 488 fluorescence dye. The dye has an adsorption peak characteristic of 495 nm and an emission peak of 519 nm. Phosphate buffer solution (PBS) is used as a buffer solution and a diluting agent. PBS is a neutral buffer solution and is used to retain suitable sample pH throughout the experiments. Isopropyl Alcohol (IPA) followed by D.I. water are used as a cleansing agents to rinse out sample from the microfluidic channels for subsequent set of experiments.

To begin, a stock solution with a working concentration of 2 mg/ml was prepared by diluting antigen with PBS. The stock solution was taken as a standard for further diluting the sample. Five different concentrations of the sample were prepared: 1×, 5×, 10×, 20× and 40× by further diluting the stock with PBS. All these samples were stored undiluted at 4° C. and protected from light as per the storage instructions.

Figure 13:
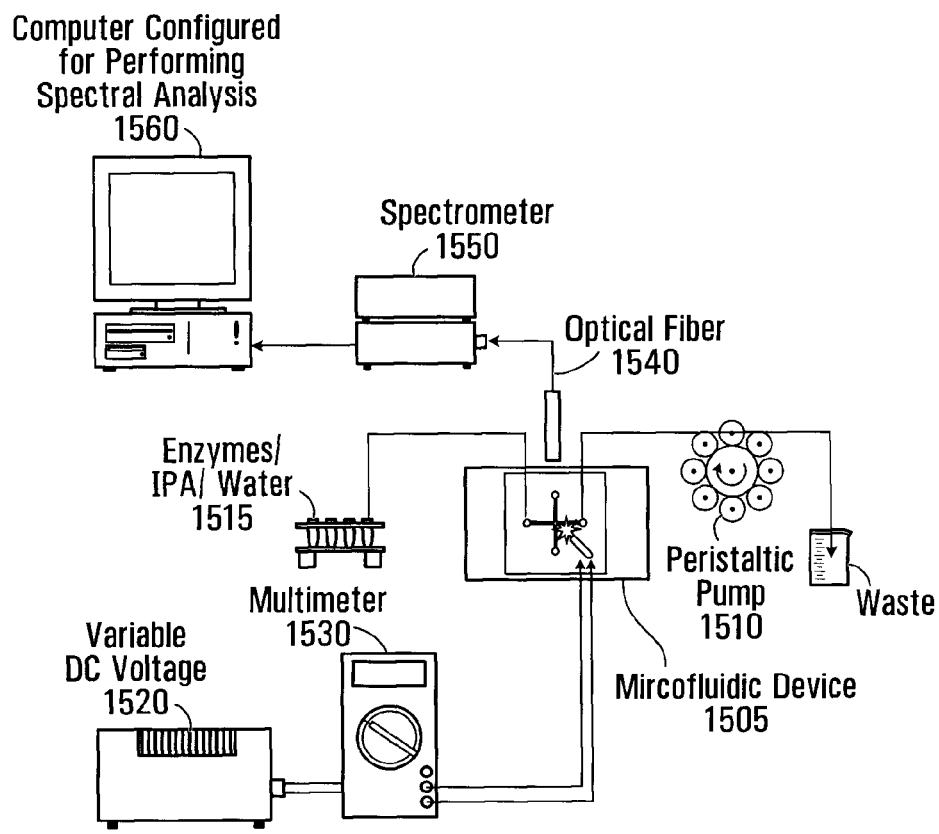
FIG. 13 is a schematic diagram of a bio-optical fluorescence detection system using a microfluidic chip according to an embodiment of the invention.

FIG. 13 is a schematic representation of a bio-optical fluorescence detection setup using an LED source in a microfluidic chip 1505 for the described testing. A Gilson Minipuls two channel peristaltic pump 1510 was used as a pumping device to pass enzymes, water and IPA 1515 throughout the experiment. The pump 1510 was connected to the outlet port of the microfluidic chip and suction pumping was adopted to pump in the samples 1515 to the chip 1505 through the inlet tube. Suction pumping not only reduces the time taken to fill in and rinse out the microfluidic chip reaction chamber by 50% but also saves precious enzymes. Two rinsing ports were connected to pump in IPA and water 1515 during rinsing steps. A variable DC voltage source 1520 was applied to the electrical connections of the LED source of the microfluidic chip 1505 and corresponding voltage was measured using a digital multimeter 1530. A detected signal was collected from the optical fiber coupled to a lens at the top of the microfluidic chip 1505. The intensity of the signal was measured in absolute units with a spectrometer 1550 and data acquisition software on a computer 1560 configured to acquire, process and display the data. The entire set of experiments was carried out in a dark environment to avoid optical noise from external sources.

Bio-Optical Detection Methodology

Detection is achieved by measuring the density of antigen within the detector area of the reaction chamber and is a colorimetric signal of fluoresced intensity towards an induced excited intensity. The emitted signal is directly proportional to the amount of detected antigen. Such a way of interpreting results using spectrometer is called as densitometric analysis. The relative fluorescence unit (RFU) intensity or voltage response detected by the spectrometer or photodiode is then compared with the calibrated standard plots to know the antigen concentration present in the sample. Bio-optical testing with integrated device is achieved for different concentrations of antigen in order to establish the sensitivity, throughput and relative fluorescence. A minimum level concentration of fluorescing signal can be detected from the prepared samples.

In the experiments, the pump speed for passing enzymes was maintained at 0.5 RPM pump speed (flow rate of 3.4 µl/min or $56.67 \times 10^{-12}$ m³/s) and the pump speed for initiating and rinsing conditions was increased to 2.5 RPM (flow rate of 17 µl/min or $283.3 \times 10^{-12}$ m³/s). Firstly, the microfluidic chip was pre-cleaned by passing diluted HCl (HCl:DI=1:5) for 300 s and followed by D.I. water mixed with 0.1% Tween 20 surfactant (Sigma Aldrich, Canada) for 300 s. Doing this not only ensured a clean and uncontaminated chip for the experiments but also retained the hydrophilic nature of the channels and chamber. PBS was then passed to initialize the experiments through inlet and rinsing ports for 300 s to initiate the experiments.

The 40× diluted sample tagged to Alexafluor 488 was pumped into the reaction chamber and the signals were detected for 470 nm and 519 nm over a time period of 600 s. Relative fluorescence units (RFU) for time acquisitions at wavelengths 470 nm/519 nm was measured for inlet flows. Excitation and fluorescence readings at the end of 600 s were recorded. The channel was flushed with IPA and then passed with PBS to initialize a next set of experiments. The procedure was repeated with 20×, 10×, 5×, 1× concentrations of the sample and finally with PBS. Normalized fluorescence with respect to 1× sample was calculated for the mentioned concentrations of sample.

Figure 14:
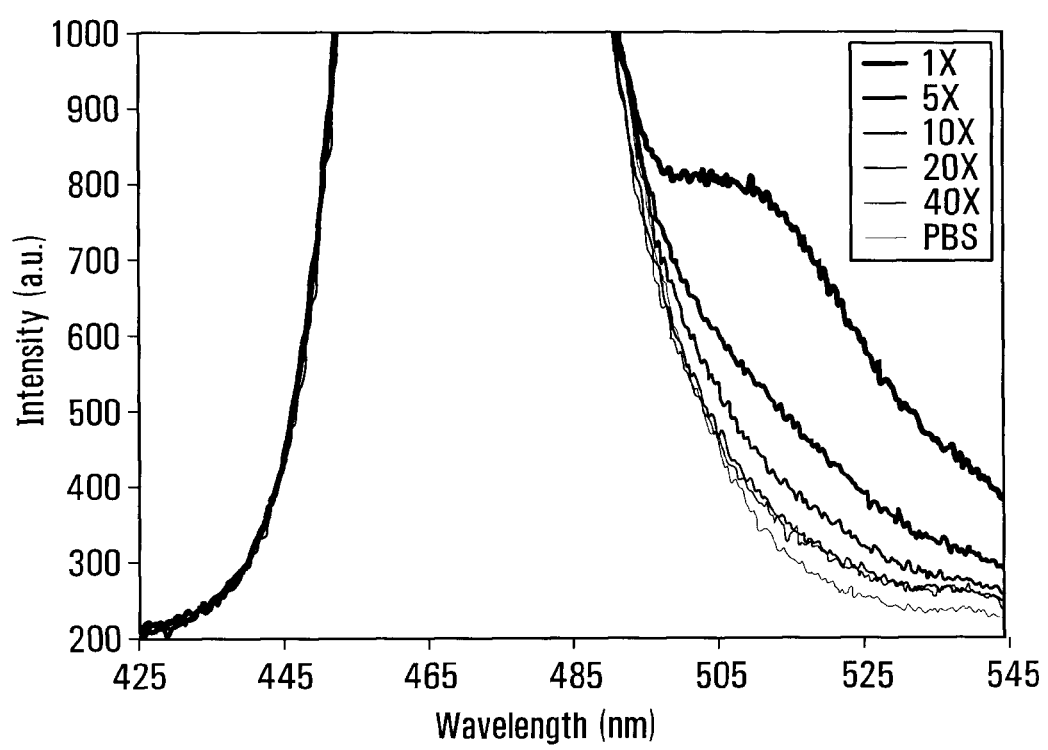
FIGS. 14, 15, 17 and 18 are graphical plots showing results from testing of a prototype microfluidic chip.

The results obtained for fluorescence detection of tagged donkey anti-sheep IgG conjugates in the microfluidic chip using LED induced excitation is given in FIG. 14 as a spectral response. It is observed that the fluorescence signal decreases with sample concentration and a minimum significant emission is observed at 40× diluted antibody donkey anti-sheep IgG conjugates.

$$\text{Minimum amont of fluorescence detected at } 40X = 50 \ \mu g/mL$$

$$\begin{aligned}\text{Minimum volume of detection} &= \text{Size of detector} * \text{depth} \\ &= \frac{\pi}{4} \times 250^2 \times 250 \\ &= 1.227 \times 10^7 \ \mu m^3 \\ &= 0.000012 \ ml \\ &= 0.012 \ \mu l\end{aligned}$$

Figure 15:
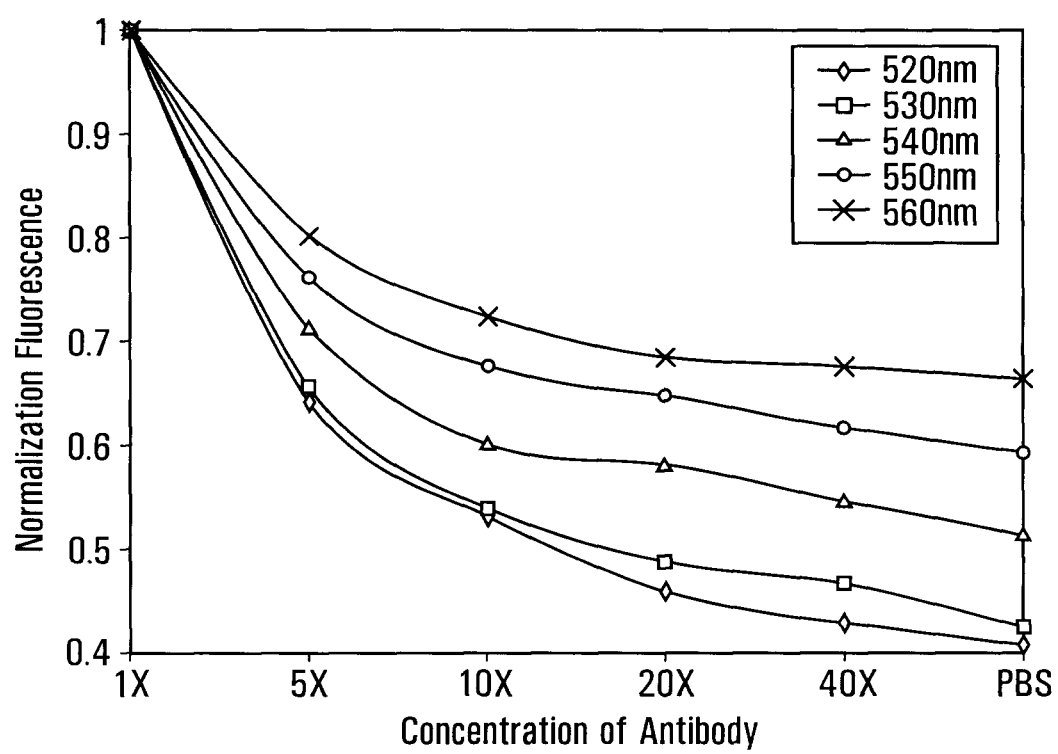

Therefore, the minimum amount of donkey anti-sheep IgG conjugates detected in the chamber=0.6 ng The fluorescence unit is normalized for different wavelengths with respect to the fluorescence observed at highest concentration of the sample. Since fluorescence is a function of emission intensity of the fluorophore, this relation will be more useful to study the effect of sensitivity against concentration and hence to detect minimum detection capacity or sensitivity of the biosensor. It can be clearly observed from FIG. 15, a graph illustrating normalized values of fluorescence, that a low concentration of antigen is detected for the dilution of 40×. Further, sensitivity of fluorescence detection decreases at 540, 550 and 560 nm plots of the graph of FIG. 15 that emission signal readings could be counted at 530 nm as well with an increase in the Stoke's gap by 10 nm.

Figure 16:
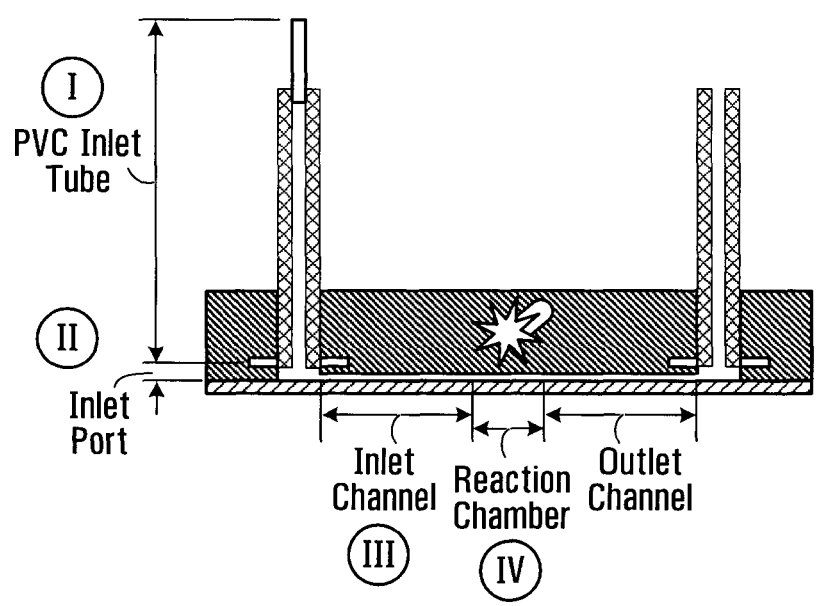
FIG. 16 is a cross sectional view of a microfluidic chip that indicates how residence time for inlet and rinsing flows were calculated during testing of the prototype microfluidic chip.

Time acquisition graphs are plotted for inlet flows and rinsing flows to understand minimum time taken for the sample to reach an optimized and constant fluorescence level. This is evaluated from the total time taken by the sample to reach the reaction chamber during inlet or rinsing flows, which are equivalent to the time ratio of the sum total volume of PVC tube (I), inlet port (II) and inlet channel (III) to the fluid rate of flow (see FIG. 16).

Thus, the time taken for the sample to reach chamber for inlet flow equals $$(I) + (II) + (III) / \text{flow rate} = \left(\frac{(3.19 + 3.8 + 0.492) \times 10^{-9}}{56.67 \times 10^{-12}}\right) = 132 \ s$$

For inlet flow at 0.5 RPM=3.4 µl/min=$56.67 \times 10^{-12}$ m³/s=$V_{avg}$=1 mm/s $$\text{Residence time in the chamber} = \frac{0.164 \times 10^{-9}}{56.67 \times 10^{-12}} = 2.9 \ s$$

Similarly, the time taken for the sample to reach chamber for rinsing flow equals $$(I) + (II) + (III) / \text{flow rate} = \left(\frac{(3.19 + 3.8 + 0.492) \times 10^{-9}}{283.3 \times 10^{-12}}\right) = 27 \ s$$

For rinsing flow at 2.5 RPM=17 µl/min=$283.3 \times 10^{-12}$ m³/s=$V_{avg}$=5 mm/s $$\text{Residence time in the chamber} = \frac{0.164 \times 10^{-9}}{283.3 \times 10^{-12}} = 0.58 \ s$$

Figure 17:
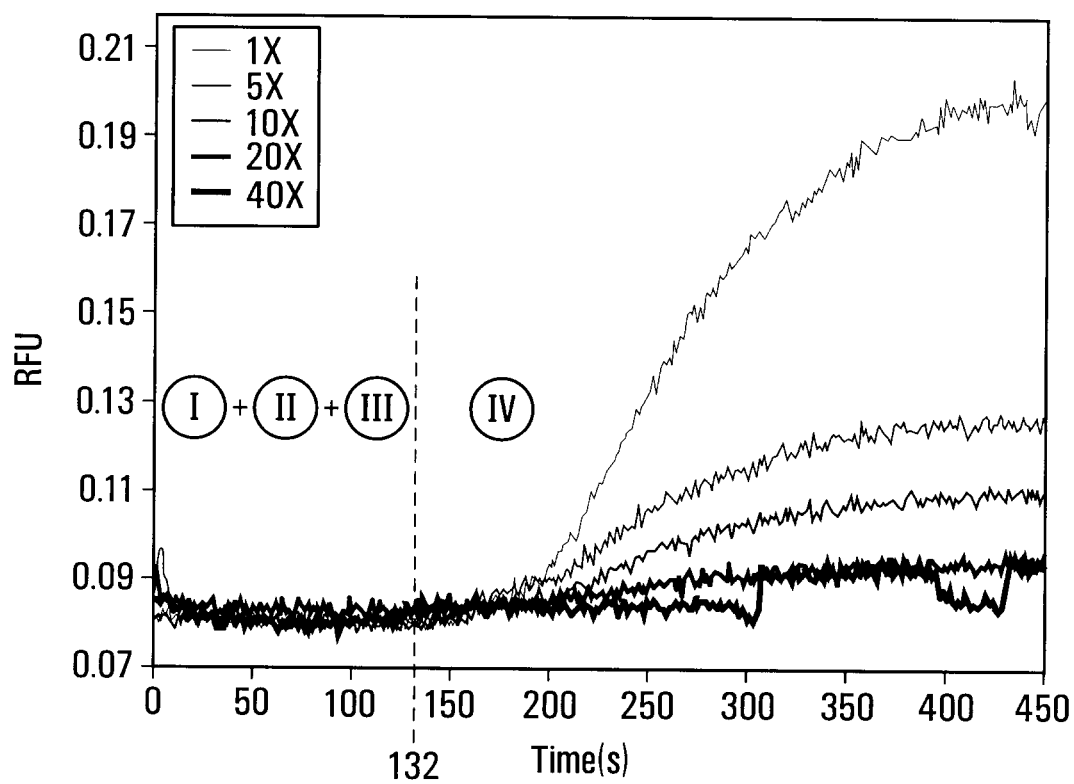
Figure 18:
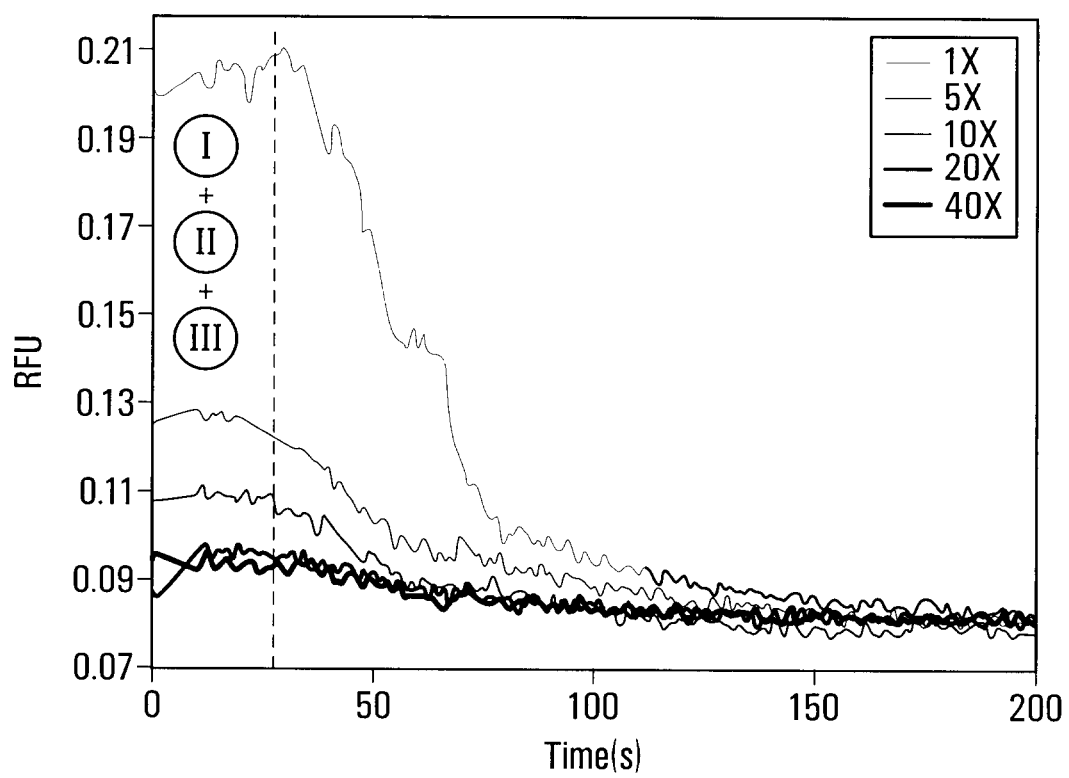

It is observed from the FIG. 17 that the change in fluorescence signal at 132 s for all the sample concentrations clearly indicates the entry of antigen into the microfluidic detection chamber. It is also observed that the total time taken from the initial run for optimum fluorescence detection is 450 s for inlet flows. Similarly, one can observe in the time acquisition graphs from FIG. 18 that the fluorescence signal starts diminishing after 27 s indicating the total time taken for the sample to reach chamber for rinsing flow. The total time taken for the microfluidic chip ready for the next set of experiments is found from the experiments to be 200 s.

Numerous modifications and variations of the present invention are possible in light of the above teachings. It is therefore to be understood that within the scope of the appended claims, the invention may be practised otherwise than as specifically described herein.

The invention claimed is:

1. A polymer-based microfluidic device for detecting induced fluorescence in a micro-volume of a fluid, the device comprising:
a multi-layer top portion comprising:
a wavelength specific excitation source for inducing fluorescence in the fluid;
a lens for collecting emitted fluorescence from the fluid; and
a micro-spectrometer for detecting light collected by the lens;
a bottom portion;
a chamber having walls bounded by the top portion and the bottom portion, the chamber configured to contain the fluid, the chamber in fluid communication with at least one inlet port for receiving the fluid and at least one outlet port for removing the fluid;
wherein the lens, the micro-spectrometer, and the chamber are in a functional layer of the multi-layer top portion, and wherein the functional layer abuts the bottom portion; and
wherein an optical path of emitted fluorescence from the chamber and an optical path of light emitted by the excitation source do not share a common path to the lens through the chamber.

2. The device of claim 1 further comprising:
a filter located between the chamber and the lens, the filter for reducing interference between the emitted fluorescence from the fluid and other spectral components.

3. The device of claim 1 further comprising at least one additional inlet port and at least one additional outlet port for use in rinsing the chamber.

4. The device of claim 1 wherein the micro-spectrometer comprises a photodetector.

5. The device of claim 1 wherein an optical waveguide is located between the lens and the micro-spectrometer.

6. The device of claim 5 wherein the optical waveguide is an optical fiber.

7. The device of claim 1 wherein the micro-spectrometer is a diffraction grating spectrometer.

8. The device of claim 1, wherein the lens is configured to couple the emitted fluorescence from the fluid into an optical fiber.

9. The device of claim 1 wherein the top portion includes at least two layers, a first layer comprising the wavelength specific excitation source and a second layer that is the functional layer comprising the lens, the micro-spectrometer and the chamber, wherein the first layer is farther away from the bottom portion than is the second layer.

10. The device of claim 1 wherein the wavelength specific excitation source is a narrow band source.

11. The device of claim 1 wherein the wavelength specific excitation source is any one of: a wavelength specific light emitting diode (LED); a wavelength specific organic LED (OLED) and a semiconductor laser.

12. The device of claim 10, wherein the narrow band source is a blue wavelength narrow band source.

13. The device of claim 1 wherein the polymer-based device is fabricated from one or more of the following:
polydimethylsiloxane (PDMS); photoresist, SUB; poly ethyl acrylate (PEA); poly methyl methacrylate (PMMA); silicon doped PDMS (PsiA); and other derivatives of these materials.

14. A method for fabricating a polymer-based microfluidic device for detecting induced fluorescence in a micro-volume of a fluid, the method comprising:
forming a top portion comprising:
integrating in a polymer-based material a wavelength specific excitation source, a lens configured to collect fluorescence emitted from the fluid; and a micro-spectrometer for detecting light collected by the lens;
forming a recess in a surface of the top portion that is a partial boundary of a chamber configured to contain the micro-volume of the fluid, the chamber comprising at least one inlet port and at least one outlet port;
bonding the surface of the top portion to a bottom portion, the bottom portion forming a remainder of the boundary of the chamber,
wherein the lens, the micro-spectrometer, and the chamber are in a functional layer of the multi-layer top portion, and wherein the functional layer abuts the bottom portion.

15. The method of claim 14 wherein forming the top portion further comprises:
integrating a filter in the polymer-based material for reducing interference between the fluorescence emitted from the fluid and other spectral components.

16. The method of claim 14 wherein integrating in the polymer-based material the wavelength specific excitation source comprises:
integrating one of: a wavelength specific light emitting diode (LED); a wavelength specific organic LED (OLED) and a semiconductor laser.

17. The method of claim 14 wherein forming the top portion comprises forming the top portion in at least two layers, a first layer comprising the wavelength specific excitation source and a second layer that is the functional layer comprising the lens, the micro-spectrometer and the chamber, wherein the first layer is farther away from the bottom portion than is the second layer.

* * * * *

UNITED STATES PATENT AND TRADEMARK OFFICE
CERTIFICATE OF CORRECTION

PATENT NO. : 8,926,906 B2  
APPLICATION NO. : 13/055364  
DATED : January 6, 2015  
INVENTOR(S) : Packirisamy et al.

It is certified that error appears in the above-identified patent and that said Letters Patent is hereby corrected as shown below:

In the Claims,

Column 22, line 11, Claim 13: "SUB" should be replaced with -- SU8 --

Signed and Sealed this  
Sixteenth Day of June, 2015

Michelle K. Lee  
*Director of the United States Patent and Trademark Office*